United States Patent
Young et al.

(10) Patent No.: US 12,018,024 B2
(45) Date of Patent: Jun. 25, 2024

(54) COMPOUNDS AND COMPOSITIONS FOR THE TREATMENT OF CRYPTOSPORIDIOSIS

(71) Applicant: Novartis AG, Basel (CH)

(72) Inventors: Joseph Michael Young, Pleasant Hill, CA (US); Michael Robert Turner, Walnut Creek, CA (US); Peichao Lu, Pleasant Hill, CA (US)

(73) Assignee: Novartis AG, Basel (CH)

( * ) Notice: Subject to any disclaimer, the term of this patent is extended or adjusted under 35 U.S.C. 154(b) by 234 days.

(21) Appl. No.: 17/499,663

(22) Filed: Oct. 12, 2021

(65) Prior Publication Data

US 2022/0112189 A1 Apr. 14, 2022

Related U.S. Application Data

(60) Provisional application No. 63/091,866, filed on Oct. 14, 2020.

(51) Int. Cl.
  *C07D 471/04* (2006.01)
  *A61K 45/06* (2006.01)
  *A61P 33/02* (2006.01)

(52) U.S. Cl.
  CPC ............ *C07D 471/04* (2013.01); *A61K 45/06* (2013.01); *A61P 33/02* (2018.01)

(58) Field of Classification Search
  CPC .... C07D 471/04; C07D 487/04; A61K 45/06; A61P 33/02; Y02A 50/30
  See application file for complete search history.

(56) References Cited

FOREIGN PATENT DOCUMENTS

| WO | 2017125898 A1 | 7/2017 | |
|---|---|---|---|
| WO | WO-2017125898 A1 * | 7/2017 | ........... A61K 31/437 |

* cited by examiner

*Primary Examiner* — Jeffrey S Lundgren
*Assistant Examiner* — Ellie Park
(74) *Attorney, Agent, or Firm* — Emily T. Wu

(57) ABSTRACT

The invention relates to compounds of Formula I:

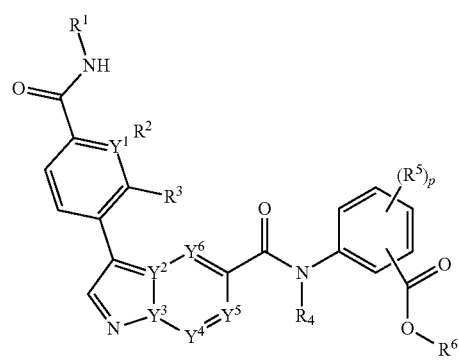

or a pharmaceutically acceptable salt, tautomer, or stereoisomer, thereof, wherein the variables are as defined herein. The present invention further provides pharmaceutical compositions comprising such compounds and methods of using such compounds for method for treating, preventing, inhibiting, ameliorating, or eradicating the pathology and/or symptomology of cryptosporidiosis by administering such a compound.

15 Claims, No Drawings

COMPOUNDS AND COMPOSITIONS FOR THE TREATMENT OF CRYPTOSPORIDIOSIS

CROSS REFERENCE TO RELATED APPLICATIONS

This application claims the benefit of priority to U.S. Provisional Patent Application No. 63/091,866 filed Oct. 14, 2020, the disclosure of which is incorporated herein by reference in its entirety.

BACKGROUND OF THE INVENTION

Field of the Invention

The invention relates to a compounds, pharmaceutical compostions comprising such compounds and methods for using such compounds for treating, preventing, inhibiting, ameliorating, or eradicating the pathology and/or symptomology of cryptosporidiosis.

Background

Globally ~6.5 million children under the age of five die each year. Diarrhoeal diseases are the second leading cause of death in children and are responsible for ~760,000 deaths in low income countries (2013). Nearly 80% of child deaths by diarrhea occur in South Asia and sub-Saharan Africa. Diarrhea is caused by a wide-range of pathogens including viral (rotavirus, norovirus etc), bacterial (Shiegella, ETEC, Vibrio, Campylobacter, etc) and protozoan parasites (Giardia, Entameoba, Cryptosporidium, etc). Rotavirus is the leading cause of diarrheal disease accounting for ~450,000 deaths but safe and effective vaccines are already available. Childhood mortality caused by a diarrhea causing protozoan parasite Cryptosporidium spp is being recognized of late (Striepen, 2013).

Apicomplexan parasites cause a range of important human diseases like malaria, cryptosporidiosis and toxoplasmosis, caused respectively by phylogenetically related parasites Plasmodium spp, Cryptosporidium spp and Toxoplasma gondii. Cryptosporidiosis affects people worldwide; it is an intestinal illness that manifests as watery diarrhea. In humans, the disease is caused by mainly two species Cryptosporidium hominis and Cryptosporidium parvum. In healthy adults, cryptosporidiosis is usually a self-limiting infection with symptoms lasting 1-2 weeks. On the contrary immunocompromised individuals are highly vulnerable to cryptosporidiosis and suffer from chronic, long-lasting life-threatening diarrhea. A recent epidemiological study investigating the cause and effect of diarrhea in children below 5 years of age identified cryptosporidiosis as the second most common pathogen responsible for severe diarrhea and is also associated with death in 12-23 months old young children (Kotioff et al., 2012). Cryptosporidium is known to cause nearly 100,000 deaths in children each year. Cryptosporidium infection is also associated with long-term growth faltering and cognitive deficiency (Kotioff et al., 2012, Striepen, 2013, Checkley et al., 2015). Cryptosporidiosis is still an underappreciated global health concern with no available vaccine and with only one FDA approved drug, Nitazoxanide (Alinia) (2003). The standard of care is sub-optimal and unproven in needy patient population, i.e., 6-18 months' old malnourished children and immunocompro-mised patients (Checkley et al., 2015). Hence there is an unmet medical need to find highly effective drugs against Cryptosporidiosis.

A major advance in understanding the molecular biology of Cryptosporidium came from the genome sequencing of C. parvum (Abrahamsen et al., 2004) and C. hominis (Xu et al., 2004). The genomes of these two closely related species are similar (96-97% identity) with ~4000 genes spread on 8 chromosomes. The genome of Cryptosporidium spp are substantially smaller than other apicomplexan protozoan parasites like Plasmodium falciparum (Gardner et al., 2002) with fewer introns and shorter non-coding regions. Although Cryptosporidium exhibit genetic divergence from other apicomplexan parasites like Plasmodium, a number of druggable molecular targets and pathways are conserved between apicomplexan protozoa (Abrahamsen et al., 2004, Xu et al., 2004).

SUMMARY OF THE INVENTION

The invention provides a compound of Formula I:

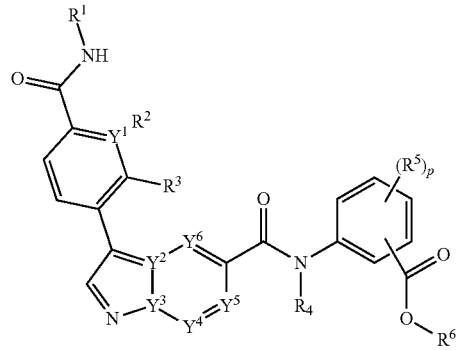

or a pharmaceutical acceptable salt, tautomer or stereoisomer thereof, wherein
p is 0, 1, 2, or 3;
each of $Y^1$, $Y^2$, $Y^3$, $Y^4$, $Y^5$, or $Y^6$ is independently C or N;
each of $R^1$, $R^2$, $R^3$ or $R^4$ is independently hydrogen or $C_{1-6}$alkyl;
each $R^5$ is independently selected from the group consisting of hydrogen, $C_{1-6}$alkyl, cyano, —C(O)$C_{1-6}$alkyl; halo, halo$C_{1-6}$alkyl, and —S(O)$_2C_{1-6}$alkyl;
$R^6$ is selected from the group consisting of:
a) hydrogen, and
b) $C_{1-6}$alkyl, unsubstituted or substituted by 1-3 substituents independently selected from the group consisting of
  i) $C_{1-6}$alkoxy,
  ii) halo,
  iii) thio$C_{1-6}$alkyl,
  iv) $C_{4-6}$heterocycloalkyl, unsubstituted or substituted by 1-3 substituents independently selected from the group consisting of oxo and $C_{1-6}$alkyl;
  v) $C_{5-6}$heteroaryl, unsubstituted or substituted by 1-3 $C_{1-6}$alkyl substituents;
  vi) —C(O)$R^7$, and
  vii) —C(O)NR$^7$R$^7$, wherein each $R^7$ is independently hydrogen or $C_{1-6}$alkyl; and processes for preparing such compounds.

In a second aspect, the present invention relates to compounds and methods and uses of compounds in the manufacture of a medicament for preventing, treating, inhibiting, ameliorating, or eradicating the pathology and/or symptomology of cryptosporidiosis by modulating the activity of phosphatidylinositol-4-OH kinase of the *Cryptosporidium* parasite.

Unless specified otherwise, the term "compound" refers to compounds of Formula (I) or subformulae thereof, salts of the compound, hydrates or solvates of the compound, as well as all stereoisomers (including diastereoisomers and enantiomers), tautomers and isotopically labeled compound (including deuterium substitutions). A compound of Formula I (or subformulae thereof) further comprise polymorphs of the compound.

DETAILED DESCRIPTION OF THE INVENTION

Definitions

For purposes of interpreting this specification, the following definitions will apply and whenever appropriate, terms used in the singular will also include the plural and vice versa.

"Acyl" as used herein refers to the radical —C(═O)$R_a$, where $R_a$ is hydrogen or a non-hydrogen substituent on the carbonyl carbon, forming different carbonyl-containing groups including, but are not limited to, acids, acid halides, aldehydes, amides, esters, and ketones.

"Alkoxy" as used herein refers the radical —O-alkyl, wherein the alkyl is as defined herein. $C_X$alkoxy and $C_{X-Y}$alkoxy as used herein describe alkoxy groups where X and Y indicate the number of carbon atoms in the alkyl chain. Representative examples of $C_{1-10}$alkoxy include, but are not limited to, methoxy, ethoxy, propoxy, 2-propoxy, butoxy, tert-butoxy, pentyloxy, hexyloxy, heptyloxy, octyloxy and decyloxy. The alkyl portion of the alkoxy may be optionally substituted, and the substituents include those described for the alkyl group below.

"Alkyl" as used herein refers to a fully saturated branched or unbranched hydrocarbon chain having up to 10 carbon atoms. $C_X$ alkyl and $C_{X-Y}$ alkyl as used herein describe alkyl groups where X and Y indicate the number of carbon atoms in the alkyl chain. For example, $C_{1-10}$ alkyl refers to an alkyl radical as defined above containing one to ten carbon atoms. $C_{1-10}$ alkyl includes, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Alkyl represented along with another radical like arylalkyl, heteroarylalkyl, alkoxyalkyl, alkoxyalkyl, alkylamino, where the alkyl portion shall have the same meaning as described for alkyl and is bonded to the other radical. For example, $(C_{6-10})$aryl$(C_{1-3})$alkyl includes, benzyl, phenylethyl, 1-phenylethyl, 3-phenylpropyl, 2-thienylmethyl, 2-pyridinylmethyl and the like.

Unless stated otherwise specifically in the specification, an alkyl group may be unsubstituted or substituted by one or more substituents to the extent that such substitution makes sense chemically. Typical substituents include, but are not limited to halo, hydroxyl, alkoxy, cyano, amino, acyl, aryl, arylalkyl, and cycloalkyl, or an heteroforms of one of these groups, and each of which can be substituted by the substituents that are appropriate for the particular group.

"Alkenyl" as used herein refers to a straight or branched, hydrocarbon chain having up to 10 carbon atoms and at least one carbon-carbon double bond. $C_X$alkenyl and $C_{X-Y}$alkenyl as used herein describe alkenyl groups where X and Y indicate the number of carbon atoms in the alkenyl chain. Examples of $C_{2-7}$alkenyl include vinyl, allyl, isopropenyl, pentenyl, hexenyl, heptenyl, 1-propenyl, 2-butenyl, 2-methyl-2-butenyl, and the like. The alkenyl may be optionally substituted, and the substituents include those described for the alkyl group descried herein.

"Alkylene" as used herein refers to a divalent alkyl group defined herein. Examples of $C_{1-10}$alkylene includes, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene. An alkylene group may be optionally substituted, and the substituents include those described for the alkyl group described herein.

"Alkynyl" as used herein refers to a straight or branched, hydrocarbon chain having up to 10 carbon atoms and at least one carbon-carbon triple bond. $C_X$alkenyl and $C_{X-Y}$alkenyl as used herein describe alkynyl groups, where X and Y indicate the number of carbon atoms in the alkynyl chain. For example, $C_{2-7}$alkenyl include, but are not limited to, ethynyl, propargyl, 3-methyl-1-pentynyl, 2-heptynyl and the like. An alkynyl may be optionally substituted, and the substituents include those described for the alkyl group described herein.

"Alkylene" as used herein refers to a divalent alkyl group defined herein. Examples of $C_{1-10}$alkylene includes, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene. An alkylene group may be optionally substituted, and the substituents include those described for the alkyl group described herein.

"Alkenylene" as used herein refers to a divalent alkenyl group defined herein. Examples of $C_{1-3}$alkenylene include, but are not limited to, ethene-1,2-diyl, propene-1,3-diyl, and methylene-1,1-diyl. An alkenylene may be optionally substituted, and the substituents include those described for the alkyl group described herein.

"Alkynylene" as used herein refers to a divalent alkynyl group defined herein. Examples of alkynylene include ethyne-1,2-diylene, propyne-1,3-diylene, and the like. An alkynylene may be optionally substituted, and the substituents include those described for the alkyl group described herein.

"Amino" as used herein refers to the radical —$NH_2$. When an amino is described as "substituted" or "optionally substituted", the term includes NR'R" wherein each R' and R" is independently H, or is an alkyl, aryl, cycloalkyl, arylalkyl, cycloalkylalkyl group or a heteroform of one of these groups, and each of the alkyl, aryl, arylalkyl or cycloalkylalkyl groups or heteroforms of one of these groups, is optionally substituted with the substituents described herein as suitable for the corresponding group.

The term "amino" also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Alkylamino" as used herein refers to the radical —NR$_a$R$_b$, where at least one of, or both, R$_a$ and R$_b$ are an alkyl group as described herein. An C$_{1-4}$alkylamino group includes —NHC$_{1-4}$ alkyl and —N(C$_{1-4}$alkyl)$_2$; e.g., —NHCH$_3$, —N(CH$_3$)$_2$, —NH(CH$_2$CH$_3$), —N(CH$_2$CH$_3$)$_2$, and the like.

"Aromatic" as used herein refers to a moiety wherein the constituent atoms make up an unsaturated ring system, where all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Aryl" as used herein refers to a 6-14 membered monocyclic or polycyclic aromatic ring assembly where all the ring atoms are carbon atoms. Typically, the aryl is a 6 membered monocyclic, a 10-12 membered bicyclic or a 14-membered fused tricyclic aromatic ring system. C$_X$aryl and C$_{X-Y}$aryl as used herein describe an aryl group where X and Y indicate the number of carbon atoms in the ring system. C$_{6-14}$aryls include, but are not limited to, phenyl, biphenyl, naphthyl, azulenyl, and anthracenyl.

An aryl may be unsubstituted or substituted by 1-5 (such as one, or two, or three) substituents independently selected from the group consisting of hydroxy, thiol, cyano, nitro, C$_{1-4}$alkyl, C$_{1-4}$alkenyl, C$_{1-4}$alkynyl, C$_{1-4}$alkoxy, thioC$_{1-4}$alkyl, C$_{1-4}$alkenyloxy, C$_{1-4}$alkynyloxy, halogen, C$_{1-4}$alkylcarbonyl, carboxy, C$_{1-4}$alkoxycarbonyl, amino, C$_{1-4}$alkylamino, di-C$_{1-4}$alkylamino, C$_{1-4}$ alkylaminocarbonyl, di-C$_{1-4}$alkylaminocarbonyl, C$_{1-4}$alkylcarbonylamino, C$_{1-4}$alkylcarbonyl(C$_{1-4}$ alkyl)amino, sulfonyl, sulfamoyl, alkylsulfamoyl, C$_{1-4}$alkylaminosulfonyl, aryl, heteroaryl, cycloalkyl and heterocycloalkyl, wherein each of the afore-mentioned substitutents may be further substituted by one or more substituents independently selected from halogen, alkyl, hydroxyl or C$_{1-4}$alkoxy groups.

When an "aryl" is represented along with another radical like "arylalkyl", "aryloxyalkyl", "aryloxycarbonyl", "aryloxy-carbonylalkyl", the aryl portion shall have the same meaning as described in the above-mentioned definition of "aryl".

"Aryloxy" as used herein, refers to the radical —O-aryl, wherein aryl is as defined herein.

"Bicyclic" or "bicyclyl" as used here in refers to a ring assembly of two rings where the two rings are fused together, linked by a single bond or linked by two bridging atoms. The rings may be a carbocyclyl, a heterocyclyl, or a mixture thereof.

"Bridging ring" as used herein refers to a polycyclic ring system where two ring atoms that are common to two rings are not directly bound to each other. One or more rings of the ring system may also comprise heteroatoms as ring atoms. Non-exclusive examples of bridging rings include norbornanyl, 7-oxabicyclo[2.2.1]heptanyl, adamantanyl, and the like.

"Carbamoyl" as used herein refers to the radical —C(O) NR$_a$— where R$_a$ is H, or is an alkyl, alkenyl, alkynyl, acyl, aryl, or arylalkyl group or a heteroform of one of these groups, and each of the alkyl, alkenyl, alkynyl, acyl, aryl, arylalkyl or heteroforms of one of these groups is optionally substituted with the substituents described herein as suitable for the corresponding group.

"Cycloalkyl", as used herein, means a radical comprising a non-aromatic, saturated or partially unsaturated, monocyclic, bicyclic, tricyclic, fused, bridged or spiro polycyclic hydrocarbon ring system of 3-20 carbon atoms. C$_X$cycloalkyl and C$_{X-Y}$cycloalkyl are typically used where X and Y indicate the number of carbon atoms in the ring assembly. For example, C$_{3-6}$cycloalkyl includes cyclopropyl, cyclobutyl, cyclopentyl, cycohexyl, cyclohexenyl, 2,5-cyclohexadienyl.

Exemplary monocyclic cycloalkyl include, but are not limited to, cyclopropyl, cyclobutyl, cyclopentyl, cyclopentenyl, cyclohexyl and cyclohexenyl and the like.

Exemplary bicyclic cycloalkyls include bornyl, norbornanyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic cycloalkyl groups include, for example, adamantyl.

A cycloalkyl may be unsubstituted or substituted by one, or two, or three, or more substituents independently selected from the group consisting of hydroxyl, thiol, cyano, nitro, oxo, alkylimino, C$_{1-4}$alkyl, C$_{1-4}$alkenyl, C$_{1-4}$alkynyl, C$_{1-4}$alkoxy, C$_{1-4}$thioalkyl, C$_{1-4}$alkenyloxy, C$_{1-4}$ alkynyloxy, halogen, C$_{1-4}$alkylcarbonyl, carboxy, C$_{1-4}$alkoxycarbonyl, amino, C$_{1-4}$alkylamino, di-C$_{1-4}$alkylamino, C$_{1-4}$alkylaminocarbonyl, di-C$_{1-4}$alkylaminocarbonyl, C$_{1-4}$alkylcarbonylamino, C$_{1-4}$ alkylcarbonyl(C$_{1-4}$alkyl)amino, sulfonyl, sulfamoyl, alkylsulfamoyl, C$_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or C$_{1-4}$alkoxy groups.

"Cycloalkylene", as used herein, refers to a divalent radical comprising a cycloalkyl ring assembly as defined herein.

"Cycloalkoxy", as used herein, refers to —O-cycloalkyl, wherein the cycloalkyl is defined herein. Representative examples of C3.12cycloalklyoxy include, but are not limited to, monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyloxy, decahydronaphthyloxy, bicyclo[2.1.1]hexyloxy, bicyclo[2.2.1]heptyloxy, bicyclo[2.2.1]heptenyloxy, 6,6-dimethylbicyclo[3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

"Cyano", as used herein, refers to the radical —CN.
"Cyano", as used herein, refers to the radical —CN.
"EC50", refers to the molar concentration of an inhibitor or modulator that produces 50% efficacy.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halo" or "halogen" as used herein refers to fluoro, chloro, bromo, and iodo.

"Haloalkyl", or halo-substituted-alkyl" as used herein, refers to an alkyl as defined herein, which is substituted by one or more halo atoms defined herein. The haloalkyl can be mono-haloalkyl, dihaloalkyl or polyhaloalkyl including per-haloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. $C_X$haloalkyl and $C_{X-Y}$haloalkyl are typically used where X and Y indicate the number of carbon atoms in the alkyl chain. Non-limiting examples of $C_{1-4}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A $C_{1-4}$perhaloalkyl group refers to a $C_{1-4}$alkyl group having all hydrogen atoms replaced with halo atoms.

"Heteroaryl", as used herein, refers to a 5-14 membered ring assembly (e.g., a 5-7 membered monocycle, an 8-10 membered bicycle, or a 13-14 membered tricyclic ring system) having 1 to 8 heteroatoms selected from N, O and S as ring atoms and the remaining ring atoms are carbon atoms. The nitrogen atoms of such heteroaryl rings can be optionally quaternized and the sulfur atoms of such heteroaryl rings can be optionally oxidized. $C_X$heteroaryl and $C_{X-Y}$heteroaryl as used herein describe heteroaryls where X and Y indicate the number of ring atoms in the heteroaryl ring. Typical $C_{5-7}$heteroaryl groups include thienyl, furanyl, imidazolyl, pyrazolyl, pyrrolyl, pyrrolinyl, thiazolyl, 1,3,4-thiadiazolyl, isothiazolyl, oxazolyl, oxadiazole isoxazolyl, triazolyl, tetrazolyl, pyridyl, pyridazinyl, pyrazinyl, pyrazinyl, pyrimidinyl, and the like. Bicyclic or tricyclic $C_{8-14}$heteroaryls include, but are not limited to, those derived from benzo[b]furan, benzo[b]thiophene, benzimidazole, imidazo[4,5-c]pyrdine, quinazoline, thieno[2,3-c]pyridine, thieno[3,2-b]pyridine, thieno[2,3-b]pyridine, quinazolinyle, pteridinyl, indolizine, imidazo[1,2a]pyridine, quinoline, quinolinyl, isoquinoline, phthalazine, quinoxaline, naphthyridine, naphthyridinyl, quinolizine, indolyl, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, purinyl, carbazole, acridine, phenazine, phenothiazene, phenoxazine, 1,2-dihydropyrrolo[3,2,1-hi]indole, indolizine, pyrido[1,2-a]indole and 2(1H)-pyridinone.

A heteroaryl may be unsubstituted or substituted with one or more substituents independently selected from hydroxyl, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$ alkoxycarbonyl, amino, $C_{1-4}$alkylamino, di-$C_{1-4}$alkylamino, $C_{1-4}$alkylaminocarbonyl, di-$C_{1-4}$ alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$ alkoxy groups.

When a heteroaryl is represented along with another radical like "heteroaryloxy", "heteroaryloxyalkyl", "heteroaryloxycarbonyl", the heteroaryl portion shall have the same meaning as described in the above-mentioned definition of "heteroaryl".

"Heteroaryloxy", as used herein, refers to an —O-heteroaryl group, wherein the heteroaryl is as defined in this Application.

"Heteroatom", as used herein, refers to an atom that is not a carbon atom. Particular examples of heteroatoms include, but are not limited to, nitrogen, oxygen, and sulfur.

"Heterocycloalkyl", as used herein, refers to a 4-20 membered, non-aromatic, saturated or partially unsaturated, monocyclic or polycyclic ring system, comprising 1-8 heteroatoms as ring atoms and that the remaining ring atoms are carbon atoms. The heteroatoms are selected from N, O, and S, preferably O and N. The nitrogen atoms of the heterocycloalkyl can be optionally quaternized and the sulfur atoms of the heterocycloalkyl can be optionally oxidized. The heterocycloalkyl can include fused or bridged rings as well as spirocyclic rings. $C_X$heterocycloalkyl and $C_{X-Y}$heterocycloalkyl are typically used where X and Y indicate the number of ring atoms in the ring. Typically, the heterocycloalkyl is 4-8-membered monocyclic ring containing 1 to 3 heteroatoms, a 7 to 12-membered bicyclic ring system containing 1-5 heteroatoms, or a 10-15-membered tricyclic ring system containing 1 to 7 heteroatoms. Examples of $C_{4-6}$heterocycloalkyl include azetidinyl, tetrahydrofuran (THF), dihydrofuran, 1, 4-dioxane, morpholine, 1,4-dithiane, piperazine, piperidine, 1,3-dioxolane, imidazolidine, imidazoline, pyrazolidinyl, pyrroline, pyrrolidine, tetrahydropyran, dihydropyran, oxathiolane, dithiolane, 1,3-dioxane, 1,3-dithiane, oxathiane, thiomorpholine, and the like A heterocycloalkyl may be unsubstituted or substituted with 1-5 substituents (such as one, or two, or three) each independently selected from hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heterocycloalkyl forms part of other groups like "heterocycloalkyl-alkyl", "heterocycloalkoxy", "heterocycloalkyl-aryl", the heteroaryl portion shall have the same meaning as described in the above-mentioned definition of "heteroaryl"

"Heterocycloalkyl fused to a phenyl" as used herein, refers to a bicyclic fused ring system that one of the ring is heterocycloalkyl as defined above and the other ring is a phenyl. A heterocycloalkyl fused to a phenyl includes but are not limited to benzo[b][1,4]oxazinyl, oxo-benzo[b][1,4]oxazinyl, tetrahydroquinoxalinyl, tetrahydroquinolinyl, indolinyl, benzo[d]imidazolyl, and the like.

"Heterocyclyl", "heterocycle" or "heterocyclo", as used herein, refers to a 3-20 membered, monocyclic or polycyclic ring system containing at least one heteroatom moiety selected from the group consisting of N, O, SO, $SO_2$, (C=O), and S, and preferably N, O, S, optionally containing one to four additional heteroatoms in each ring. $C_X$heterocyclyl and $C_{X-Y}$heterocyclyl are typically used where X and Y indicate the number of ring atoms in the ring system. Unless otherwise specified, a heterocyclyl may be saturated, partially unsaturated, aromatic or partially aromatic.

"Hydroxy", as used herein, refers to the radical —OH.

"Hydroxyalkyl" or "hydroxyl-substituted alkyl" as used herein, refers to an alkyl as defined herein, having one or more of the available hydrogen of the alkyl replaced by a hydroxyl group. For example, a hydroxy$C_{1-4}$alkyl includes, but are not limited to, —$CH_2CH_2OH$, —CH(OH)$CH_2CH_2OH$, —CH(OH)$CH_2CH(OH)CH_3$.

"Nitro", as used herein, refers to the radical —$NO_2$.

"Oxo", as used herein, refers to the divalent radical =O

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, Protecting Groups in Organic Synthesis, 3rd edition, John Wiley & Sons, Inc. 1999.

"Unsubstituted or substituted" or "optionally substituted" as used herein indicate the substituent bound on the available valance of a named group or radical. "Unsubstituted" as used herein indicates that the named group or radical will have no further non-hydrogen substituents. "Substituted" or "optionally substituted" as used herein indicates that at least one of the available hydrogen atoms of named group or radical has been (or may be) replaced by a non-hydrogen substituent.

"Substituted terminally" as used herein referred to a substituent replacing a hydrogen at a terminal position of the parent molecule. For example $C_{1-4}$alkyl substituted terminally by an amino means —$C_{1-4}$alkylene-amino, which includes —($CH_2$)—$NH_2$, —($CH_2$)$_2$—$NH_2$, —($CH_2$)—$NH_2$, —($CH_2$)$CH_2$($CH_2$—$NH_2$), —($CH_2$)4-$NH_2$, —C($CH_2$)($CH_2CH_2$—$NH_2$), —C($CH_3$)$_2$($CH_2$—$NH_2$), and the like.

Unless otherwise specified, examples of substituents may include, but are not limited to, halo, nitro, cyano, thio, oxy, hydroxy, carbonyloxy, $C_{1-6}$alkoxy, $C_{6-10}$aryloxy, hetero$C_{5-10}$aryloxy, carbonyl, oxycarbonyl, aminocarbonyl, amino, $C_{1-6}$alkylamino, sulfonamido, imino, sulfonyl, sulfinyl, $C_{1-6}$alkyl, $C_{1-6}$haloalkyl, hydroxy$C_{1-6}$alkyl, carbonyl$C_{1-6}$alkyl, thiocarbonyl$C_{1-10}$alkyl, sulfonyl$C_{1-6}$alkyl, sulfinyl$C_{1-6}$alkyl, $C_{1-10}$ azaalkyl, imino$C_{1-6}$alkyl, $C_{3-12}$cycloalkyl$C_{1-6}$alkyl, $C_{4-15}$heterocycloalkyl$C_{1-6}$alkyl, Caj oaryl$C_{1-6}$alkyl, $C_{5-10}$heteroaryl$C_{1-6}$alkyl, $C_{10-12}$bicycloaryl$C_{1-6}$alkyl, $C_{9-12}$heterobicycloaryl$C_{1-6}$alkyl, $C_{3-12}$cycloalkyl, $C_{4-12}$heterocycloalkyl, $C_{4-12}$bicycloalkyl, $C_{3-12}$heterobicycloalkyl, $C_{4-12}$aryl, hetero$C_{1-10}$aryl, $C_{9-12}$bicycloaryl and $C_{4-12}$heterobicycloaryl. "Sulfamoyl" as used herein refers to the radical —S(O)2NRaRb where Ra and Rb are independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl groups or heteroforms of one of these groups, is optionally substituted with the substituents described herein as suitable for the corresponding group.

"Sulfanyl" as used herein, means the radical —S—.

"Sulfinyl", as used herein, means the radical —S(O)—. It is noted that the term "sulfinyl" when referring to a monovalent substituent can alternatively refer to a substituted sulfinyl group, S(=O)R, where R is hydrogen or a non-hydrogen substituent on the sulfur atom forming different sulfinyl groups including sulfinic acids, sulfinamides, sulfinyl esters, and sulfoxides.

"Sulfonyl", as used herein, means the radical —S(O)2-. It is noted that the term "sulfonyl" when referring to a monovalent substituent can alternatively refer to a substituted sulfonyl group, S(=O)2R, where R is hydrogen or a non-hydrogen substituent on the sulfur atom forming different sulfonyl groups including sulfonic acids, sulfonamides, sulfonate esters, and sulfones.

"Thiocarbonyl", as used herein, refers to the radical —C(=S)—. It is noted that the term thiocarbonyl when referring to a monovalent substituent can alternatively refer to a substituted thiocarbonyl group, C(=S)R, where R is hydrogen or a non-hydrogen substituent on the carbon atom forming different thiocarbonyl groups including thioacids, thioamides, thioesters, and thioketones.

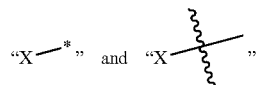

are symbols denoting the point of attachment of X, to other part of the molecule.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

It is noted in regard to all of the definitions provided herein that the definitions should be interpreted as being open ended in the sense that further substituents beyond those specified may be included. Hence, a C1alkyl indicates that there is one carbon atom but does not indicate what are the substituents on the carbon atom. Hence, a $C_1$alkyl comprises methyl (i.e., —$CH_3$) as well as —$CR_aR_bR_c$ where $R_a$, $R_b$, and $R_c$ may each independently be hydrogen or any other substituent where the atom attached to the carbon is not a hydrogen atom. Hence, —$CF_3$, —$CH_2OH$ and —$CH_2CN$, for example, are all $C_1$alkyls.

DESCRIPTION OF THE PREFERRED EMBODIMENTS

The invention provides a novel class of compounds, pharmaceutical compositions comprising such compounds and methods of using such compounds to treat or prevent diseases or disorders associated with a parasite. In particular, the compounds can be used to treat cryptosporidiosis.

In one embodiment, the compounds of the invention are of Formula I:

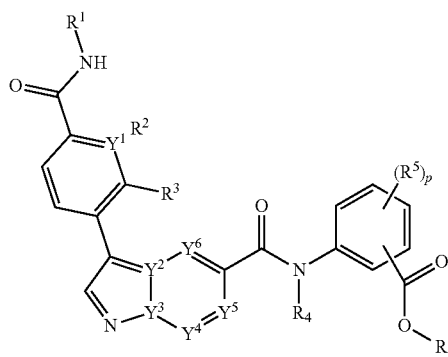

or a pharmaceutical acceptable salt, tautomer or stereoisomer thereof, wherein p is 0, 1, 2, or 3;
each of $Y^1$, $Y^2$, $Y^3$, $Y^4$, $Y^5$, or $Y^6$ is independently C or N;
each of $R^1$, $R^2$, $R^3$ or $R^4$ is independently hydrogen or $C_{1-6}$alkyl;
each $R^5$ is independently selected from the group consisting of hydrogen, $C_{1-6}$alkyl, cyano, —C(O)$C_{1-6}$alkyl; halo, halo$C_{1-6}$alkyl, and —S(O)$_2C_{1-6}$alkyl;
$R^6$ is selected from the group consisting of:
a) hydrogen, and
b) $C_{1-6}$alkyl, unsubstituted or substituted by 1-3 substituents independently selected from the group consisting of
i) $C_{1-6}$alkoxy,
ii) halo,
iii) thio$C_{1-6}$alkyl,
iv) $C_{4-6}$heterocycloalkyl, unsubstituted or substituted by 1-3 substituents independently selected from the group consisting of oxo and $C_{1-6}$alkyl;
v) $C_{5-6}$heteroaryl, unsubstituted or substituted by 1-3 $C_{1-6}$alkyl substituents;
vi) —C(O)$R^7$, and
vii) —C(O)N$R^7R^7$, wherein each $R^7$ is independently hydrogen or $C_{1-6}$alkyl.

In one embodiment of the compounds of the invention, with reference to Formula I, $Y^2$ and $Y^5$ is N and $Y^1$, $Y^3$, $Y^4$, and $Y^6$ is C.

In another variation, $Y^3$ and $Y^5$ is N and $Y^1$, $Y^2$, $Y^4$, and Ye is C.

In another variation, $Y^3$ is N and $Y^1$, $Y^2$, $Y^4$, $Y^5$, and Ye is C.

In a particular embodiment of the compounds of the invention, or a pharmaceutical acceptable salt, tautomer or stereoisomer thereof, the compound is of Formula Ia

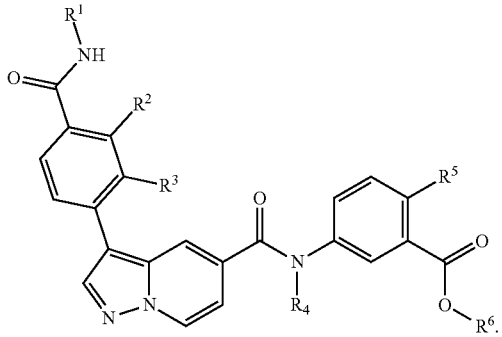

Ia

In one variation of the compounds of the present invention, with reference to the particular embodiment above, $R^1$, $R^2$ and $R^3$ is hydrogen and $R^4$ is $C_{1-6}$alkyl.

In another variation of the compounds of the present invention, with reference to the particular embodiment and any one of the variations above, $R^4$ is methyl.

In still another variation of the compounds of the present invention, with reference to the particular embodiment or any one of the variations above, $R^5$ is halo.

In still another variation of the compounds of the present invention, with reference to the particular embodiment or any one of the variations above, $R^5$ is chloro.

Particular examples of compounds or a pharmaceutically acceptable salt, tautomer or stereoisomer thereof, according to the present invention include, but are not limited to:

Methyl 5-((tert-butoxycarbonyl)amino)-2-chlorobenzoate;
tert-Butyl 5-(3-(4-carbamoylphenyl)-N-methylpyrazolo[1,5-a]pyridine-5-carboxamido)-2-chlorobenzoate;
5-(3-(4-Carbamoylphenyl)-N-methylpyrazolo[1,5-a]pyridine-5-carboxamido)-2-chlorobenzoic acid;
2-(Methylthio)ethyl 5-(3-(4-carbamoylphenyl)-N-methylpyrazolo[1,5-a]pyridine-5-carboxamido)-2-chlorobenzoate;
Isobutyl 5-(3-(4-carbamoylphenyl)-N-methylpyrazolo[1,5-a]pyridine-5-carboxamido)-2-chlorobenzoate;
2-Methoxy-2-oxoethyl 5-(3-(4-carbamoylphenyl)-N-methylpyrazolo[1,5-a]pyridine-5-carboxamido)-2-chlorobenzoate;
Thiazol-5-ylmethyl 5-(3-(4-carbamoylphenyl)-N-methylpyrazolo[1,5-a]pyridine-5-carboxamido)-2-chlorobenzoate;
2-Morpholinoethyl 5-(3-(4-carbamoylphenyl)-N-methylpyrazolo[1,5-a]pyrdine-5-carboxamido)-2-chlorobenzoate;
Ethyl 5-(3-(4-carbamoylphenyl)-N-methylpyrazolo[1,5-a]pyridine-5-carboxamido)-2-chlorobenzoate;
2,2,2-Trifluoroethyl 5-(3-(4-carbamoylphenyl)-N-methylpyrazolo[1,5-a]pyridine-5-carboxamido)-2-chlorobenzoate;
2-Methoxyethyl 5-(3-(4-carbamoylphenyl)-N-methylpyrazolo[1,5-a]pyridine-5-carboxamido)-2-chlorobenzoate;
2-(Dimethylamino)-2-oxoethyl 5-(3-(4-carbamoylphenyl)-N-methylpyrazolo[1,5-a]pyridine-5-carboxamido)-2-chlorobenzoate
Isopropyl 5-(3-(4-carbamoylphenyl)-N-methylpyrazolo[1,5-a]pyridine-5-carboxamido)-2-chlorobenzoate;
rac-1-((Ethoxycarbonyl)oxy)ethyl 5-(3-(4-carbamoylphenyl)-N-methylpyrazolo[1,5-a]pyridine-5-carboxamido)-2-chlorobenzoate;
rac-(Tetrahydrofuran-2-yl)methyl 5-(3-(4-carbamoylphenyl)-N-methylpyrazolo[1,5-a]pyridine-5-carboxamido)-2-chlorobenzoate;
Methyl 2-chloro-5-(N-methyl-3-(4-(methylcarbamoyl)phenyl)pyrazolo[1,5-a]pyridine-5-carboxamido)benzoate;
t-Butyl 2-chloro-5-(N-methyl-3-(4-(methylcarbamoyl)phenyl)pyrazolo[1,5-a]pyridine-5-carboxamido)benzoate;
2-Chloro-5-(N-methyl-3-(4-(methylcarbamoyl)phenyl)pyrazolo[1,5-a]pyridine-5-carboxamido)benzoic acid;
2-Morpholinoethyl 2-chloro-5-(N-methyl-3-(4-(methylcarbamoyl)phenyl)pyrazolo[1,5-a]pyridine-5-carboxamido)benzoate;
(5-Methyl-2-oxo-1,3-dioxol-4-yl)methyl 2-chloro-5-(N-methyl-3-(4-(methylcarbamoyl)phenyl)pyrazolo[1,5-a]pyridine-5-carboxamido)benzoate;
Methyl 2-chloro-5-(N-methyl-3-(2-methyl-4-(carbamoyl)phenyl)pyrazolo[1,5-a]pyridine-5-carboxamido)benzoate;
Methyl 2-chloro-5-(N-methyl-3-(3-methyl-4-(carbamoyl)phenyl)pyrazolo[1,5-a]pyridine-5-carboxamido)benzoate;
Methyl 5-(3-(4-carbamoylphenyl)pyrazolo[1,5-a]pyridine-5-carboxamido)-2-chlorobenzoate;
Methyl 2-chloro-5-(3-(4-(methylcarbamoyl)phenyl)pyrazolo[1,5-a]pyridine-5-carboxamido)benzoate;
Methyl 5-(3-(4-carbamoylphenyl)-N-methylpyrazolo[1,5-a]pyridine-5-carboxamido)-2-(trifluoromethoxy)benzoate;
Methyl 5-(N-methyl-3-(4-(methylcarbamoyl)phenyl)pyrazolo[1,5-a]pyrdine-5-carboxamido)-2-(trifluoromethoxy)benzoate;

Methyl 5-(3-(4-carbamoylphenyl)-N-methylpyrazolo[1,5-a]pyridine-5-carboxamido)-2-cyanobenzoate;

Methyl 2-chloro-5-(N-methyl-3-(4-(methylcarbamoyl)phenyl)imidazo[1,2-a]pyrazine-6-carboxamido)benzoate;

Methyl 2-chloro-5-(N-methyl-3-(4-(methylcarbamoyl)phenyl)pyrazolo[1,5-c]pyrimidine-5-carboxamido)benzoate; and Methyl 2-(3-(4-carbamoylphenyl)-N-methylpyrazolo[1,5-a]pyrdine-5-carboxamido)-5-chlorobenzoate.

It is noted that the compounds of the present invention may be in the form of a pharmaceutically acceptable salt. It is further note that the compounds of the present invention may be a mixture of stereoisomers, or the compound may comprise a single stereoisomer.

Further compounds of the invention are detailed in the Examples, infra.

In another aspect, the present invention is directed to a pharmaceutical composition which includes as an active ingredient a compound according to any one of the above embodiments and variations in combination with a pharmaceutically acceptable carrier, diluent or excipient.

In one embodiment, the pharmaceutical composition further includes a second agent which can be a kinase inhibitor, or an anti-inflammatory agent.

In another embodiment, the pharmaceutical composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In yet another embodiment, the pharmaceutical composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the present application is directed to a compound or a pharmaceutical composition according to any one of the above embodiments and variations for use in a therapeutic application.

In another aspect, the present application is directed to a compound or a pharmaceutical composition according to any one of the above embodiments and variations for use as a medicament.

In yet another aspect, the present invention is directed to methods for preventing, inhibiting, ameliorating, or eradicating the pathology and/or symptomology of cryptosporidiosis caused by a protozoans of the genus *Cryptosporidium*; particularly, *Cryptosporidium hominis* and *Cryptosporidium parvum*. Selected compounds were effective in minimizing the cytopathic effect of *Cryptosporidium* infection, reducing the infection rate. The inventors further demonstrated the compounds target phosphatidylinositol-4-OH kinase (PI(4)K), a lipid kinase of the cryptosporidium.

Particular compound or a pharmaceutically acceptable salt, tautomer or stereoisomer thereof, useful in the method of the current invention is selected from Table I below:

TABLE I

Listing of Compounds

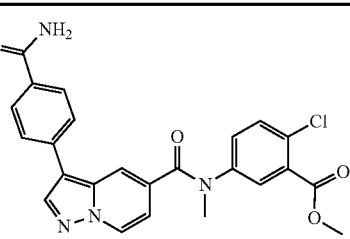

1.01

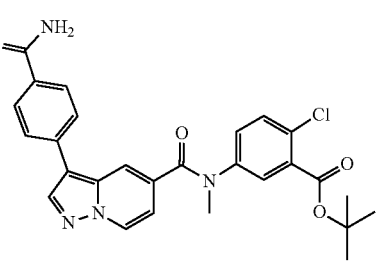

1.02

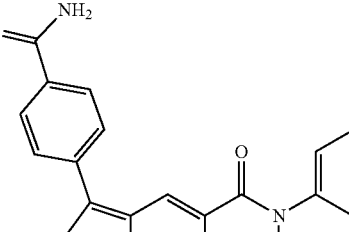

1.03

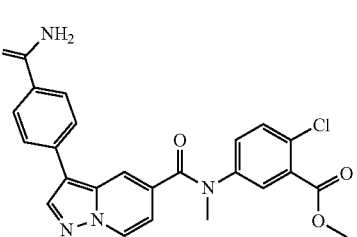

1.04

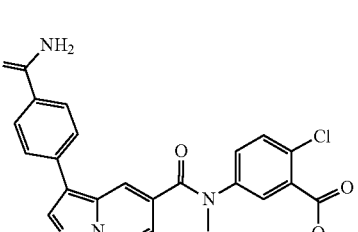

1.05

TABLE I-continued
Listing of Compounds
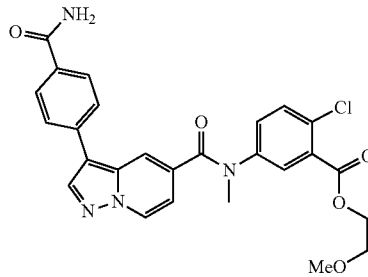

TABLE I-continued

Listing of Compounds 1.16, 1.17, 1.18, 1.19, 1.20, 1.21, 1.22, 1.23, 1.24, 1.25, 1.26

TABLE I-continued

Listing of Compounds

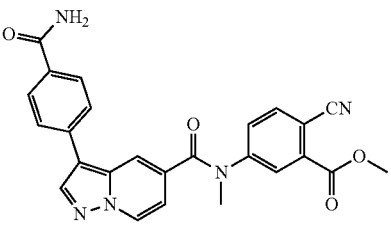 [SMILES: COC(=O)c1cc(N(C)C(=O)c2ccn3ncc(-c4ccc(C(N)=O)cc4)c3c2)ccc1C#N]
1.27

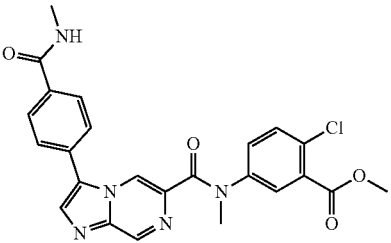 [SMILES: CNC(=O)c1ccc(-c2cnc3cnc(C(=O)N(C)c4ccc(Cl)c(C(=O)OC)c4)cn23)cc1]
2.1

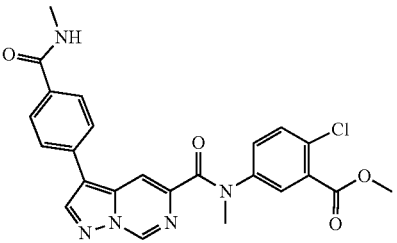 [SMILES: CNC(=O)c1ccc(-c2cnn3cnc(C(=O)N(C)c4ccc(Cl)c(C(=O)OC)c4)cc23)cc1]
3.1

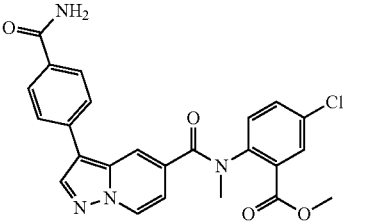 [SMILES: COC(=O)c1cc(Cl)ccc1N(C)C(=O)c1ccn2ncc(-c3ccc(C(N)=O)cc3)c2c1]
4.1

It is noted that the compounds useful in the method of the present invention may be in the form of a pharmaceutically acceptable salt. It is further note that the compounds useful in the method present invention may be a mixture of stereoisomers, or the compound may comprise a single stereoisomer.

In another aspect, the method of the present invention is directed to use of a pharmaceutical composition which includes as an active ingredient a compound according to any one of the above embodiments and variations in combination with a pharmaceutically acceptable carrier, diluent or excipient.

In another embodiment, the pharmaceutical composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In yet another embodiment, the pharmaceutical composition is adapted for administration by a route selected from the group consisting of orally, parenterally, intraperitoneally, intravenously, intraarterially, transdermally, sublingually, intramuscularly, rectally, transbuccally, intranasally, liposo- mally, via inhalation, vaginally, intraoccularly, via local delivery (for example by catheter or stent), subcutaneously, intraadiposally, intraarticularly, and intrathecally.

In another aspect, the present application is directed to a compound or a pharmaceutical composition according to any one of the above embodiments and variations for use in a therapeutic application.

In another aspect, the present application is directed to a compound or a pharmaceutical composition according to any one of the above embodiments and variations for use as a medicament.

ENUMERATED EMBODIMENTS

Various enumerated embodiments of the invention are described herein. It will be recognized that features specified in each embodiment may be combined with other specified features to provide further embodiments of the present invention.

In a first embodiment, the invention provides a compound according to Formula I,

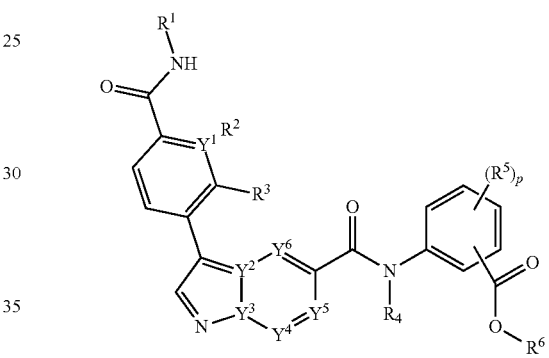

or a pharmaceutical acceptable salt, tautomer or stereoisomer thereof, wherein p is 0, 1, 2, or 3;

each of $Y^1$, $Y^2$, $Y^3$, $Y^4$, $Y^5$, or $Y^6$ is independently C or N;

each of $R^1$, $R^2$, $R^3$ or $R^4$ is independently hydrogen or $C_{1-6}$alkyl;

each $R^5$ is independently selected from the group consisting of hydrogen, $C_{1-6}$alkyl, cyano, —C(O)$C_{1-6}$alkyl; halo, halo$C_{1-6}$alkyl, and —S(O)$_2$$C_{1-6}$alkyl;

$R^6$ is selected from the group consisting of a) hydrogen, and b) $C_{1-6}$alkyl, unsubstituted or substituted by 1-3 substituents independently selected from the group consisting of i) $C_{1-6}$alkoxy,
 ii) halo,
 iii) thio$C_{1-6}$alkyl,
 iv) $C_{4-6}$heterocycloalkyl, unsubstituted or substituted by 1-3 substituents independently selected from the group consisting of oxo and $C_{1-6}$alkyl;
 v) $C_{5-6}$heteroaryl, unsubstituted or substituted by 1-3 $C_{1-6}$alkyl substituents;
 vi) —C(O)$R^7$, and
 vii) —C(O)NR$^7$R$^7$, wherein each $R^7$ is independently hydrogen or $C_{1-6}$alkyl.

Embodiment 2. The compound according to embodiment 1, wherein $Y^3$ is N and $Y^1$, $Y^2$, $Y^4$, $Y^5$, and $Y^6$ is C.

Embodiment 3. The compound according embodiment 1, wherein $Y^3$ and $Y^5$ is N and $Y^1$, $Y^2$, $Y^4$, and $Y^6$ is C.

Embodiment 4. The compound according to embodiment 1, wherein $Y^2$ and $Y^5$ is N and $Y^1$, $Y^3$, $Y^4$, and $Y^6$ is C.

Embodiment 5. The compound according to any one of embodiments 1-4, wherein the compound is capable of inhibiting or modulating the activity of a phosphatidylinositol-4-OH kinase (PI4K) of the cryptosporidium protozoa.

Embodiment 6. The compound according to any one of embodiments 1 to 5, wherein the cryptosporidium protozoa is *Cryptosporidium hominis* or *Cryptosporidium parvum*.

Embodiment 7. The compound according to embodiment 1, wherein the compound is of Formula Ia

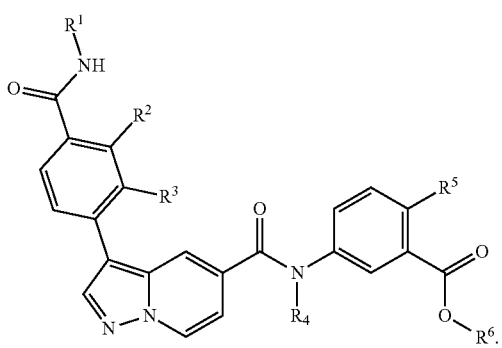

Ia

Embodiment 8. The compound according to any one of embodiments 1 to 7, wherein $R^1$, $R^2$ and $R^3$ is hydrogen and $R^4$ is $C_{1-6}$alkyl.

Embodiment 9. The compound according to any one of embodiments 1 to 8, wherein $R^4$ is methyl.

Embodiment 10. The compound of embodiment 1, wherein $R^5$ is halo.

Embodiment 11. The compound of embodiment 10, wherein $R^5$ is chloro.

Embodiment 12. The compound according to embodiment 1, wherein the compound is selected from the group of compounds listed in Table I.

Embodiment 13. A compound for treating, inhibiting, ameliorating, or eradicating the pathology and/or symptomology of cryptosporidiosis caused by a cryptosporidium protozoa, comprising administering to a patient in need thereof a therapeutically effective amount of an agent capable of modulating or inhibiting the activity of a phosphatidylinositol-4-OH kinase (PI4K) of said protozoa.

Embodiment 14. The compound of embodiment 13, wherein the cryptosporidium protozoa is *Cryptosporidium hominis* or *Cryptosporidium parvum*.

Embodiment 15. The compound of embodiment 13 or 14, wherein the agent is a compound is a compound according to any one of embodiments 1 to 12.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S.

Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Plasdmodium or (ii) associated with Plasdmodium activity, or (iii) characterized by activity (normal or abnormal) of Plasdmodium or (2) reduce or inhibit the activity of Plasdmodium; or (3) reduce or inhibit the growth of Plasdmodium. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Plasdmodium; or at least partially reducing or inhibiting the growth of Plasdmodium.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In general, compounds useful for the method of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

EXAMPLES

The present invention is further exemplified, but not to be limited, by the following examples and intermediates that illustrate the preparation of compounds of the invention. It is understood that if there appears to be a discrepancy between the name and structure of a particular compound, the structure is to be considered correct as the compound names were generated from the structures.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LC-MS Methods

Method 1:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) $H_2O$+0.025% TFA and (B) Acetonitrile+0.025% TFA. Gradient: 0.4 mL/minute, initial 15% B ramp to 95% B over 3.0 minutes, then hold until 4.0 minutes, return to 15% B at 4.1 minutes until end of run, then equilibrated the column for 2.0 minutes; MS Scan: 100 to 1000amu in 0.5 seconds per channel; Diode Array Detector: 200 nm and 400 nm.

Method 2:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) $H_2O$+0.025% TFA and (B) Acetonitrile+0.025% TFA. Gradient: 0.4 mL/minute, initial 20% B ramp to 90% B over 2.0 minutes, then hold until 4.0 minutes, return to 20% B at 4.1 minutes until end of run, then equilibrated the column for 2.0 minutes; MS Scan: 100 to 1000amu in 0.5 seconds per channel; Diode Array Detector: 200 nm and 400 nm.

Method 3:

Waters Acquity Binary Gradient Pump; Waters Acquity PDA Detector. Waters Auto sampler; Waters Acquity Evaporative Light Scattering Detector; Waters Quattro micro API Mass Spectrometer with ESI and APCI ion source; UPLC Column: Waters Acquity; BEH; C18 1.7 um 100×2.1 mm; Mobile Phase: (A) $H_2O$+0.025% TFA and (B) Acetonitrile+0.025% TFA. Gradient: 0.3 mL/minute, initial 10% B ramp to 80% B over 4.0 minutes, then hold until 6.0 minutes, return to 10% B at 6.1 minutes until end of run, then equilibrated the column for 2.5 minutes; MS Scan: 100 to 1000amu in 0.5 seconds per channel; Diode Array Detector: 200 nm and 400 nm; Drift tube temperature: 50° C. and N2 gas flow:40Psi for ELSD Detector.

Method 4:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) H2O+0.025% TFA and (B) Acetonitrile+0.025% TFA. Gradient: 0.4 mL/minute, initial 20% B ramp to 80% B over 2.0 minutes, then hold until 4.0 minutes, return to 20% B at 4.1 minutes until end of run, then equilibrated the column for 2.0 minutes; MS Scan: 100 to 1000amu in 0.5 seconds per channel; Diode Array Detector: 200 nm and 400 nm Method 5:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) H2O+0.025% TFA and (B) Acetonitrile+0.025% TFA. Gradient: 0.4 mL/minute, initial 10% B ramp to 80% B over 3.0 minutes, then hold until 4.0 minutes, return to 20% B at 4.1 minutes until end of run, then equilibrated the column for 2.0 minutes; MS Scan: 100 to 1000amu in 0.5 seconds per channel; Diode Array Detector: 200 nm and 400 nm Method 6:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters X-Terra; MS; C18; 2.5 um 50×4.6 mm; Mobile Phase: (A) 0.01M Ammonium Bicarbonate in Water and (B) Acetonitrile; Gradient 1 mL/minute, initial 50% B, ramp to 80% B over 4.0 minutes, and hold until 6.0 minutes, return to 50% B at 6.1 minutes until end of run. The column is re-equilibrated for 3 minutes. MS Scan: 100 to 1200amu; Diode Array Detector 200 nm-400 nm.

Method 7:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters X-Bridge; C18; 3.5 um 150×4.6 mm; Mobile Phase: (A) 0.01M Ammonium Bicarbonate in Water and (B) Acetonitrile; Gradient: 1 mL/minute, initial 20% B, ramp to 80% B over 4.0 minutes, and hold until 8.0 minutes, return to 20% B at 8.1 minutes until end of run. The column is re-equilibrated for 3 minutes. MS Scan: 100 to 1200amu; Diode Array Detector: 200 nm-400 nm.

Method 8:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters Symmetry; C18; 3.5 um 75×4.6 mm; Mobile Phase: (A) H$_2$O+0.1% Formic acid and (B) Acetonitrile+0.1% Formic acid; Gradient: 1 mL/minute, initial 20% B, ramp to 80% B over 4.0 minutes, and hold until 7.0 minutes, return to 20% B at 7.1 minutes until end of run. The column is re-equilibrated for 3 minutes. MS Scan: 100 to 1200amu; Diode Array Detector: 200 nm-400 nm.

Example 1.01: N-(4-cyanophenyl)-N-methyl-3-(4-(trifluoromethyl)phenyl)pyrazolo[1,5-a]pyridine-5-carboxamide

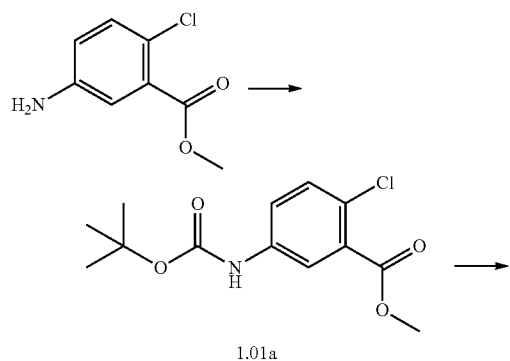

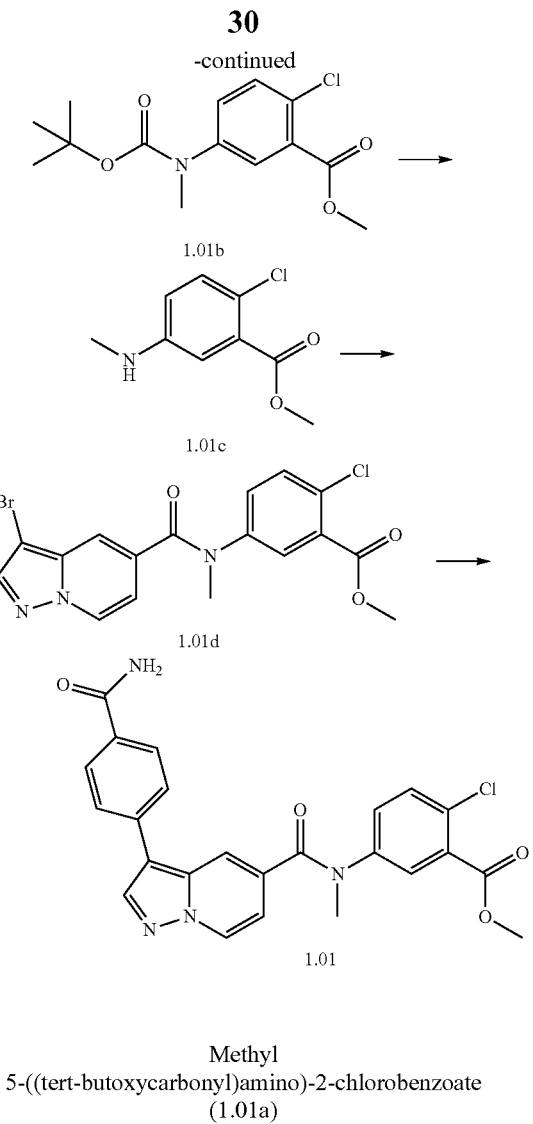

Methyl 5-((tert-butoxycarbonyl)amino)-2-chlorobenzoate (1.01a)

A 500 mL flask was charged with charged with methyl 5-amino-2-chlorobenzoate (58.6 g, 316 mmol) and water (250 ml). The mixture was heated to 33° C. on an aluminum block. Boc$_2$O (76 g) was added slowly and the flask fitted with a septum. At 3 h, additional Boc$_2$O (7.6 g) was added. After 30 min, the mixture was cooled to rt and filtered. The solids were washed with water (150 mL) and dried on a frit, followed by drying in oven at 35° C. for 12 h to yield 1.01a (87.6 g, 307 mmol, 97% yield) as a brown solid. LC-MS (m/z): 230.1 [M+H]$^+$, RT=0.91 min. $^1$H NMR (500 MHz, Chloroform-d) δ 7.83 (d, J=2.7 Hz, 1H), 7.51-7.45 (m, 1H), 7.35 (d, J=8.7 Hz, 1H), 6.55 (s, 1H), 3.92 (s, 3H), 1.52 (s, 9H).

Methyl 5-((tert-butoxycarbonyl)(methyl)amino)-2-chlorobenzoate (1.01b)

1.01a (87.6 g, 307 mmol) was divided evenly into three 500 mL flasks equipped with stirbars. MeCN (100 mL) was added to each. The flasks were cooled to 0° C. and Cs$_2$CO$_3$ (66.6 g) was added to each flask. After 15 min, iodomethane (13 mL) was added to each flask and the ice baths removed. At 5 h, iodomethane (2 mL) was added and the slurries stirred overnight. The mixtures were combined, diluted with EtOAc (300 mL) and washed with water and brine. Heptane (100 mL) was added to the organic layer and the solution dried over Na$_2$SO$_4$, filtered and concentrated to provide 1.01b (94 g, 314 mmol, 102% yield) as a brown oil. LC-MS (m/z): 244.2 [M+H]$^+$, RT=0.94 min. $^1$H NMR (500 MHz, Chloroform-d) δ 7.72 (d, J=2.5 Hz, 1H), 7.38 (d, J=8.6 Hz, 1H), 7.33 (t, J=5.6 Hz, 1H), 3.92 (s, 3H), 3.25 (s, 3H), 1.45 (s, 9H).

Methyl 2-chloro-5-(methylamino)benzoate hydrochloride (1.01c)

1.01b (94 g, 314 mmol) was divided evenly between three 250 mL flasks. Dioxane (50 mL) was added to each flask. 4.0 M HCl in dioxane (80 mL) was added to each flask. The mixtures were stirred overnight. The mixtures were combined and concentrated in vacuo at 8 torr and 40° C. The resultant solid was suspended in in toluene (250 mL) and then concentrated at 8 torr, 50° C. The resultant powder was dried overnight at 1 torr, 35° C. to provide 1.01c (70.6 g, 299 mmol, 95% yield) as a brown solid. LC-MS (m/z): 200.1 [M+H]$^+$, RT=0.55 min. $^1$H NMR (500 MHz, DMSO-d$_6$) δ 7.27 (d, J=8.7 Hz, 1H), 6.99 (d, J=2.8 Hz, 1H), 6.80 (dd, J=8.9, 2.8 Hz, 1H), 3.82 (s, 3H), 2.69 (s, 3H).

Methyl 5-(3-bromo-N-methylpyrazolo[1,5-a]pyridine-5-carboxamido)-2-chlorobenzoate (1.01d)

To a solution of 3-bromopyrazolo[1,5-a]pyridine-5-carboxylic acid (87.0 g, 360 mmol) in DCM (1.9 L) was added oxalyl chloride (48.1 g) followed by DMF (1.39 mL) dropwise. The mixture was stirred for 5 h. NEt$_3$ (127 g) was added followed by 1.01c (76.6 g) and the mixture was stirred for 3 h. The mixture was concentrated to give a residue. The residue was purified by column chromatography (SiO$_2$, 1% to 66% Pet ether/EtOAc) to provide 1.01a (115 g, 272 mmol, 75.3% yield) as a yellow solid. LC-MS (m/z): 422.0 [M+H]$^+$, RT=0.884 min. $^1$H NMR (400 MHz, DMSO-d$_6$) δ 8.65 (d, J=7.20 Hz, 1H) 8.19 (s, 1H) 7.84 (d, J=0.80 Hz, 1H) 7.57 (s, 1H) 7.50 (s, 2H) 6.81 (d, J=6.40 Hz, 1H) 3.82 (s, 3H) 3.40 (s, 3H).

Methyl 5-(3-(4-carbamoylphenyl)-N-methylpyrazolo[1,5-a]pyridine-5-carboxamido)-2-chlorobenzoate (1.01)

To a solution of (4-carbamoylphenyl)boronic acid (54.6 g) and 1.01d (100 g, 236 mmol) in THF (2480 mL) and water (468 mL) was added PdCl$_2$(tbdpf) (7.71 g) under N$_2$. NEt$_3$ (98.7 mL) was added to the above mixture. The mixture was stirred at 53° C. for 3 h. The reaction mixture was concentrated under reduced pressure to give a residue. The residue was purified by column chromatography twice times (SiO$_2$, 1-10% MeOH in DCM). The product was triturated with methanol (500 mL) for 1 h, filtered, and purified by re-crystallization from 10/1 DCM/MeOH (400 mL) at 50° C. Compound 1.01 (41.0 g, 86.7 mmol, 36.6% yield) was obtained as a yellow solid. LC-MS (m/z): 463.1 [M+H]$^+$, RT=0.816 min. $^1$H NMR (400 MHz, DMSO-d$_6$) δ 8.67 (d, J=7.15 Hz, 1H) 8.46 (s, 1H) 8.01-7.97 (m, 1H) 7.96-7.92 (m, 2H) 7.91-7.84 (m, 2H) 7.58-7.48 (m, 4H) 7.38-7.31 (m, 1H) 6.91-6.84 (m, 1H) 3.41 (s, 3H) 3.81 (s, 3H).

Example 1-02

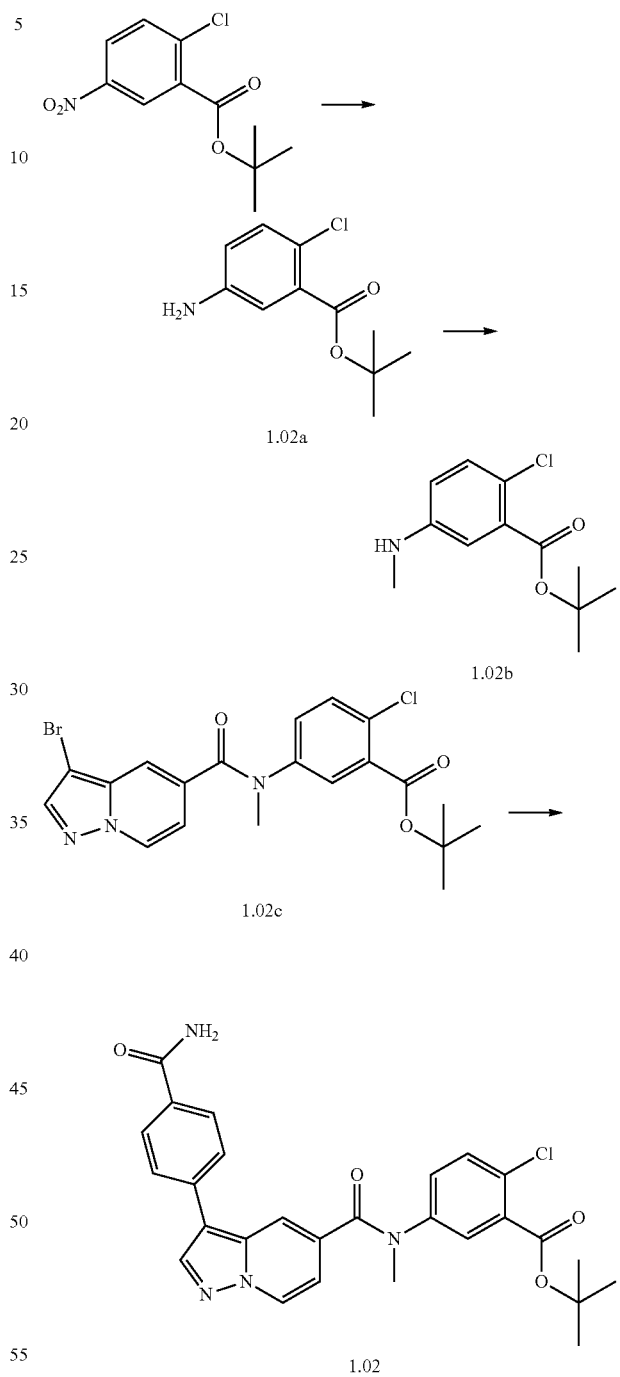

tert-Butyl 5-amino-2-chlorobenzoate (1.02a)

tert-Butyl 2-chloro-5-nitrobenzoate (10.5 g, 40.8 mmol) was taken up in 4:1 THF:water (50 mL). Saturated aqueous ammonium chloride (21.8 g) and zinc (26.7 g) were added. The mixture was stirred at 65° C. for 3h. After cooling to rt, the reaction mixture was filtered over diatomaceous earth. The filtrate was diluted with water and extracted with EtOAc. The combined organic layers were washed with brine, dried over Na$_2$SO$_4$, filtered and concentrated. The crude material was purified by flash column chromatography (24 g SiO$_2$, 10-15% EtOAc in hexane) to provide 1.02a (7 g, 30.8 mmol, 75.5%). LC-MS (m/z): 228 [M+H]$^+$, RT=1.53 min.

tert-Butyl 2-chloro-5-(methylamino)benzoate (1.02b)

1.02a (7.0 g, 30.8 mmol) was taken up in dioxane (50 mL). Cu(OAc)$_2$ (14.0 g) and pyridine (8.3 mL) were added and the mixture stirred for 30 min. Methyl boronic acid (4.54 g) was added and the mixture heated to 100° C. for 12 h. After cooling to rt, the mixture was filtered through diatomaceous earth, concentrated, and purified by flash column chromatography (24 g SiO$_2$, 5-10% EtOAc in hexane) to provide 1.02b (3.0 g, 12 mmol, 41%). LC-MS (m/z): 242 [M+H]$^+$, RT=2.4 min.

tert-Butyl 5-(3-bromo-N-methylpyrazolo[1,5-a]pyridine-5-carboxamido)-2-chlorobenzoate (1.02c)

To a solution of 3-bromopyrazolo[1,5-a]pyridine-5-carboxylic acid (3.89 g) in DCM (25 mL), oxalyl chloride (2.74 mL) and DMF (0.5 mL) were added at 0° C. The reaction mixture was stirred for 1 h at rt. The solvent was evaporated under reduced pressure. The resulting solid was dissolved in DCM (15 mL). 1.02b (3.0 g, 12.4 mmol) was dissolved in DCM (10 ml) and DIPEA (8.5 mL). This reaction mixture was added to the above acid chloride mixture at 0° C. slowly. The reaction mixture was stirred at rt for 4h. The reaction was quenched with water and extracted with DCM. The combined organic layers were washed with brine, dried over Na2SO4, filtered and concentrated. The crude solid was purified by flash column chromatography (24 g SiO$_2$, 10-20% EtOAc in hexane) to provide 1.02c (2.8 g, 3.03 mmol, 49%). LC-MS (m/z): 465.9 [M+H]$^+$, RT=2.45 min.

tert-Butyl 5-(3-(4-carbamoylphenyl)-N-methylpyrazolo[1,5-a]pyridine-5-carboxamido)-2-chlorobenzoate (1.02)

To a solution of (4-carbamoylphenyl)boronic acid (42 mg) and 1.02c (80 mg, 0.172 mmol) in 9:1 dioxane:water (8 mL) was added Cs$_2$CO$_3$ (0.167) under argon. PdCl$_2$(dppf) (14 mg) was added. The mixture was stirred at 80° C. for 3 h. The reaction mixture was poured into water and extracted with EtOAc. The combined organics were washed with brine, dried over Na$_2$SO$_4$, filtered and concentrated. The residue was purified by HPLC (Kinetex EVO, 150 mm×21.2 mm, 20 mL/min, A=0.1% TFA in water, B=MeCN, 20-40% B over 3 min, 40-70% B over 5 min) to provide compound 1.02 (23 mg, 0.045 mmol, 27% yield) was obtained as a solid. LC-MS (m/z): 505.0 [M+H]$^+$, RT=1.454 min. H NMR (400 MHz, DMSO-d$_6$) δ 8.68 (d, J=7.2 Hz, 1H), 8.49 (s, 1H), 8.01 (s, 1H), 7.98-7.93 (m, 2H), 7.91 (s, 1H), 7.69-7.65 (m, 1H), 7.58 (d, J=8.1 Hz, 2H), 7.54 (d, J=1.7 Hz, 2H), 7.38 (s, 1H), 6.83 (d, J=7.5 Hz, 1H), 3.43 (s, 3H), 1.39 (s, 9H).

Example 1-03

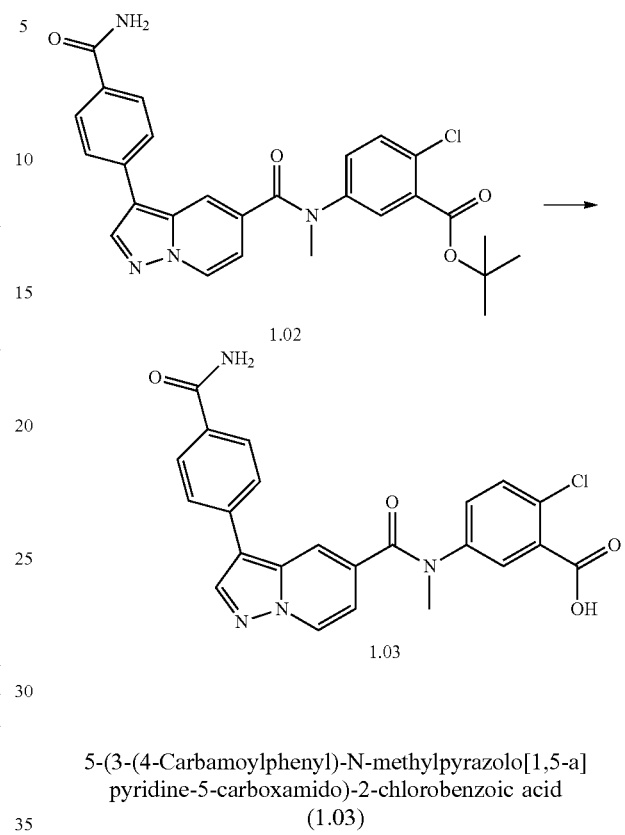

5-(3-(4-Carbamoylphenyl)-N-methylpyrazolo[1,5-a]pyridine-5-carboxamido)-2-chlorobenzoic acid (1.03)

1.02 (550 mg, 1.1 mmol) was taken up in DCM (5.0 mL). The solution was cooled to 0° C. and TFA (5.0 mL) was added. The mixture was stirred at rt for 6 h and the volatiles were removed in vacuo. The resulting solid was washed with Et$_2$O and purified by HPLC (Kinetex EVO, 150 mm×21.2 mm, 20 mL/min, A=0.1% TFA in water, B=MeCN, 15-25% B over 2 min, 25-40% B over 5 min) to provide 1.03 (190 mg, 0.42 mmol, 39%) as a solid. LC-MS (m/z): 449.05 [M+H]$^+$, RT=1.37 min. $^1$H NMR (300 MHz, DMSO-d$_6$) δ 8.69 (d, J=7.2 Hz, 1H), 8.48 (s, 1H), 8.03-7.92 (m, 3H), 7.91-7.82 (m, 2H), 7.56 (d, J=8.1 Hz, 2H), 7.50 (d, J=3.1 Hz, 2H), 7.39 (s, 1H), 6.88 (dd, J=7.1, 1.7 Hz, 1H), 3.42 (s, 3H).

Example 1-04

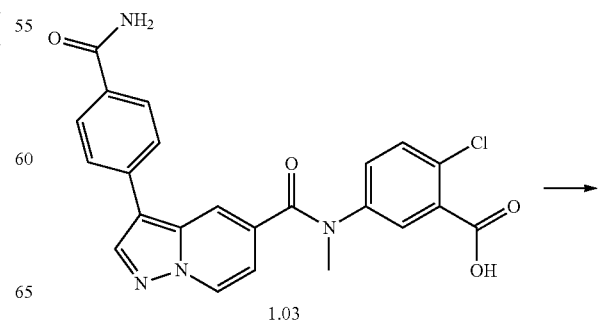

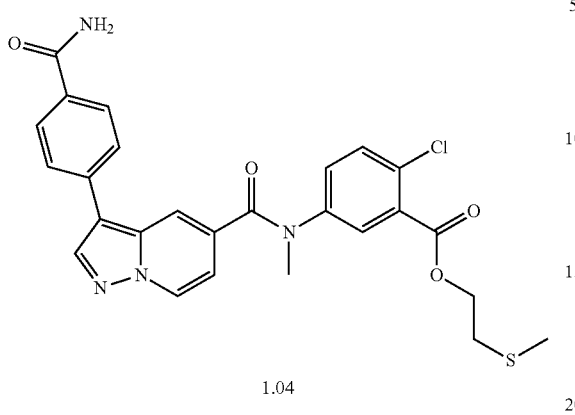

1.04

2-(Methylthio)ethyl 5-(3-(4-carbamoylphenyl)-N-methylpyrazolo[1,5-a]pyridine-5-carboxamido)-2-chlorobenzoate (1.04)

A flask was charged with 1.03 (0.1 g, 0.22 mmol), DMF (1 mL), DIPEA (0.037 mL), 3-(methylthio)propan-ol (7 mg), and HATU (33 mg). The mixture was stirred 12 h, diluted with ice water and extracted with EtOAc. The combined organic layers were washed with brine, dried over Na$_2$SO$_4$, filtered, and concentrated. The residue was purified by HPLC (Zorbax C18, 150 mm×21.2 mm, 18 mL/min, A=0.02% TFA in water, B=MeCN, 20-30% B over 2 min, 30-50% B over 7 min) to provide 1.04 (12 mg, 0.037 mmol, 18%) as a solid. LC-MS (m/z): 537.0 [M+H]$^+$, RT=1.41 min. $^1$H NMR (400 MHz, Chloroform-d) δ 8.40 (dd, J=7.3, 0.9 Hz, 1H), 8.17 (s, 1H), 7.96-7.88 (m, 2H), 7.77 (d, J=2.7 Hz, 1H), 7.65-7.60 (m, 1H), 7.42 (d, J=8.5 Hz, 1H), 7.36-7.30 (m, 2H), 7.14 (dd, J=8.5, 2.7 Hz, 1H), 6.94 (dd, J=7.3, 1.9 Hz, 1H), 6.46 (bs, 1H), 5.86 (bs, 1H), 4.46 (t, J=6.3 Hz, 2H), 3.56 (s, 3H), 2.61 (t, J=7.1 Hz, 2H), 2.11 (s, 3H), 2.05 (p, J=6.8 Hz, 2H).

Example 1-05

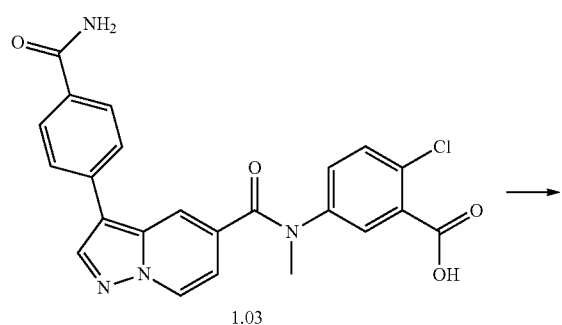

1.03

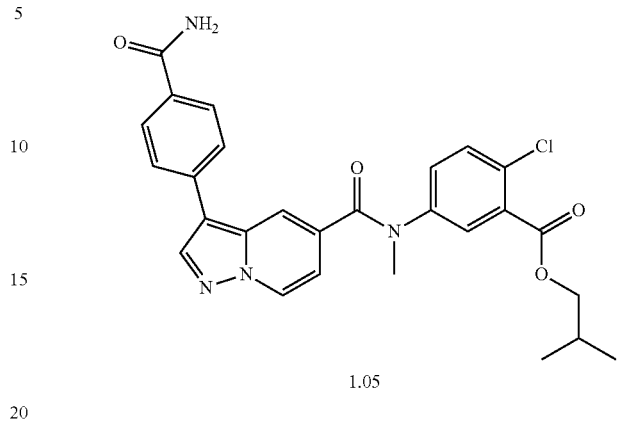

1.05

Isobutyl 5-(3-(4-carbamoylphenyl)-N-methylpyrazolo[1,5-a]pyridine-5-carboxamido)-2-chlorobenzoate (1.05)

A flask was charged with 1.03 (50 mg, 0.111 mmol), DMF (1 mL), DIPEA (0.1 mL), 2-methylpropanol (35 mg), and HATU (84 mg). The mixture was stirred 12 h, diluted with ice water and extracted with EtOAc. The combined organic layers were washed with brine, dried over Na$_2$SO$_4$, filtered, and concentrated. The residue was purified by HPLC (Zorbax C18, 150 mm×21.2 mm, 18 mL/min, A=0.02% TFA in water, B=MeCN, 10-20% B over 2 min, 20-50% B over 7 min) to provide 1.05 (15 mg, 0.037 mmol, 30%) as a solid. LC-MS (m/z): 505.0 [M+H]$^+$, RT=1.47 min. $^1$H NMR (400 MHz, Chloroform-d) δ8.39 (d, J=7.2 Hz, 1H), 8.17 (s, 1H), 7.98-7.89 (m, 2H), 7.74 (d, J=2.7 Hz, 1H), 7.64 (d, J=1.7 Hz, 1H), 7.44 (d, J=8.5 Hz, 1H), 7.36-7.30 (m, 2H), 7.16 (dd, J=8.5, 2.8 Hz, 1H), 6.93 (dd, J=7.3, 1.9 Hz, 1H), 6.51 (bs, 1H), 6.03 (bs, 1H), 4.11 (d, J=6.5 Hz, 2H), 3.56 (s, 3H), 2.03 (dq, J=13.4, 6.8 Hz, 1H), 0.96 (d, J=6.7 Hz, 6H).

Example 1-06

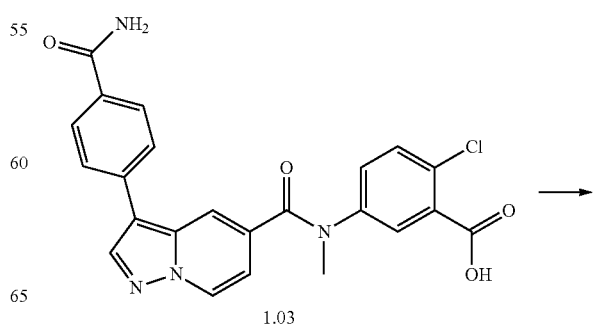

1.03

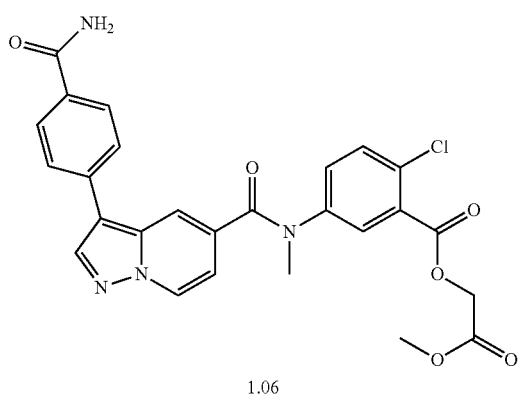

1.06

2-Methoxy-2-oxoethyl 5-(3-(4-carbamoylphenyl)-N-methylpyrazolo[1,5-a]pyridine-5-carboxamido)-2-chlorobenzoate (1.06)

A flask containing a mixture of 1.03 (70 mg, 0.16 mmol) and DMF (1.5 mL) at 0° C. was charged with $K_2CO_3$ (64 mg) and methyl 2-bromoacetate (48 mg). The mixture was stirred at 80° C. for 2 h. After cooling to rt, the mixture was diluted with ice water and extracted with EtOAc.

The combined organic layers were washed with brine, dried over $Na_2SO_4$, filtered, and concentrated. The residue was purified by HPLC (Zorbax C18, 150 mm×21.2 mm, 18 mL/min, A=0.02% TFA in water, B=MeCN, 10-20% B over 2 min, 20-50% B over 7 min) to provide 1.06 (16 mg, 0.030 mmol, 12%) as a solid. LC-MS (m/z): 521.0 [M+H]$^+$, RT=0.768 min. $^1$H NMR (400 MHz, Chloroform-d) δ 8.43 (dd, J=7.3, 1.0 Hz, 1H), 8.17 (s, 1H), 7.98 (d, J=2.7 Hz, 1H), 7.95-7.88 (m, 2H), 7.59-7.54 (m, 1H), 7.41 (d, J=8.5 Hz, 1H), 7.29-7.26 (m, 2H), 7.11 (dd, J=8.6, 2.7 Hz, 1H), 7.05-6.99 (m, 1H), 6.62 (bs, 1H), 5.89 (bs, 1H). 4.90 (s, 2H), 3.81 (s, 3H), 3.57 (s, 3H).

Example 1-07

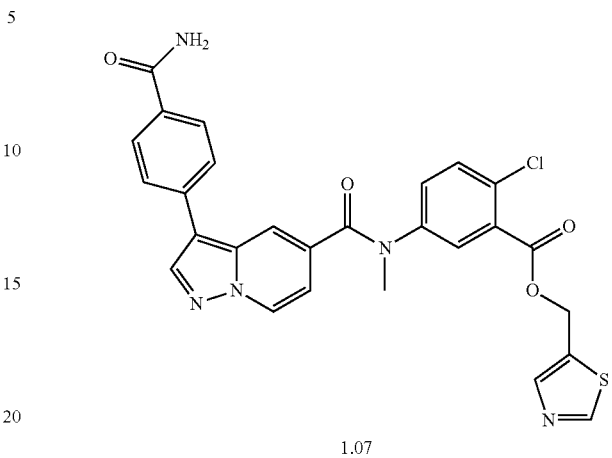

1.07

Thiazol-5-ylmethyl 5-(3-(4-carbamoylphenyl)-N-methylpyrazolo[1,5-a]pyridine-5-carboxamido)-2-chlorobenzoate (1.07)

A flask was charged with 1.03 (0.1 g, 0.222 mmol), DMF (2 mL), DIPEA (0.037 mL), thiazol-5-ylmethanol (7 mg), and HATU (33 mg). The mixture was stirred 12 h, diluted with ice water and extracted with EtOAc. The combined organic layers were washed with brine, dried over $Na_2SO_4$, filtered, and concentrated. The residue was purified by HPLC (Gemini NX, 150 mm×21.2 mm, 18 mL/min, A=0.1% TFA in water, B=MeCN, 20-30% B over 2 min, 30-45% B over 7 min) to provide 1.07 (20 mg, 0.036 mmol, 17%) as a solid. LC-MS (m/z): 549.9 [M+H]$^+$, RT=0.66 min. $^1$H NMR (400 MHz, Chloroform-d) δ8.86 (s, 1H), 8.37 (dd, J=7.3, 0.9 Hz, 1H), 8.17 (s, 1H), 7.97 (s, 1H), 7.93-7.87 (m, 2H), 7.71 (d, J=2.7 Hz, 1H), 7.63 (s, 1H), 7.42 (d, J=8.5 Hz, 1H), 7.38-7.31 (m, 2H), 7.15 (dd, J=8.6, 2.7 Hz, 1H), 6.88 (dd, J=7.3, 1.9 Hz, 1H), 5.57 (s, 2H), 3.53 (s, 3H).

Example 1-08

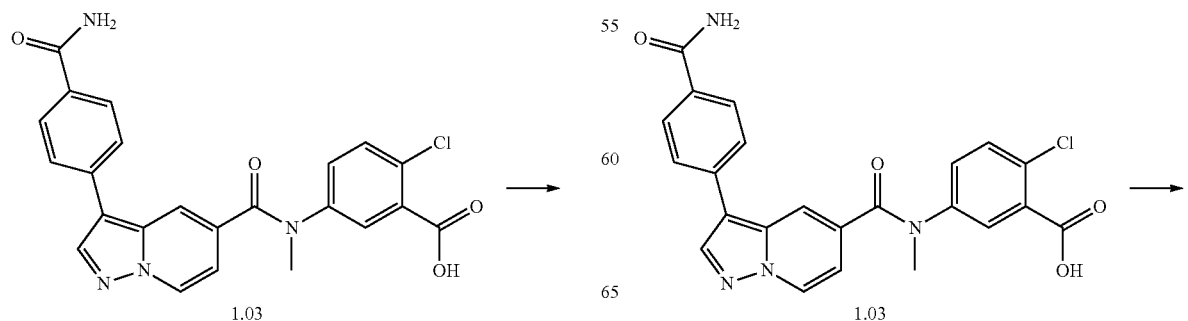

1.03

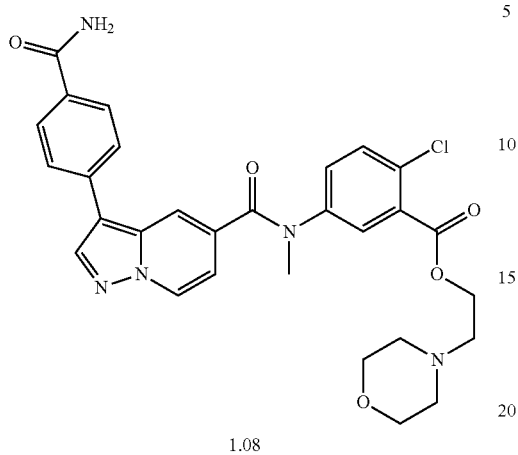

1.08

2-Morpholinoethyl 5-(3-(4-carbamoylphenyl)-N-methylpyrazolo[1,5-a]pyrdine-5-carboxamido)-2-chlorobenzoate (1.08)

A flask at 0° C. was charged with 1.03 (160 mg, 0.36 mmol), DMF (2 mL), DIPEA (0.130 mg), and HATU (270 mg). After 20 min, 4-(2-hydroxyethyl)morpholine (140 mg) was added. The mixture was stirred at rt for 4 h, diluted with ice water and extracted with EtOAc. The combined organic layers were washed with brine, dried over Na$_2$SO$_4$, filtered, and concentrated. The residue was purified by HPLC (Waters Xbridge, 150 mm×21.2 mm, 14 mL/min, A=0.02% NH$_4$OH in water, B=MeCN, 10-20% B over 2 min, 20-40% B over 7 min) to provide 1.08 (35 mg, 0.0062 mmol, 17%) as a solid. LC-MS (m/z): 562.3 [M+H]$^+$, RT=1.28 min. $^1$H NMR (400 MHz, Chloroform-d) δ 8.37 (d, J=7.6, 1.0 Hz, 1H), 8.15 (s, 1H), 7.90 (d, J=8.4 Hz, 2H) 7.73 (d, J=2.4 Hz, 1H), 7.61 (s, 1H), 7.40 (d, J=8.8 Hz, 1H), 7.31 (d, J=8.4 Hz, 1H), 7.25-7.10 (m, 1H), 7.95-7.91 (m, 1H), 4.46 (t, J=6.0 Hz, 2H), 3.65 (t, J=4.84 Hz, 4H), 3.53 (s, 3H), 2.71 (t, J=6.0 Hz, 2H), 2.50 (t, J=4.4 Hz, 4H).

Example 1-09

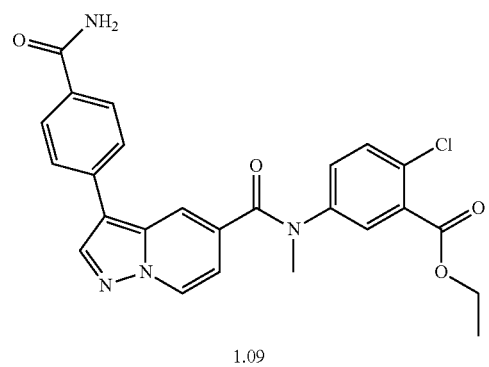

1.09

Ethyl 5-(3-(4-carbamoylphenyl)-N-methylpyrazolo[1,5-a]pyridine-5-carboxamido)-2-chlorobenzoate (1.09)

A flask containing a mixture of 1.03 (50 mg, 0.111 mmol) and DMF (1.5 mL) at 0° C. was charged with K$_2$CO$_3$ (46 mg) and iodoethane (34 mg). The mixture was stirred for 12 h, then diluted with ice water and extracted with EtOAc. The combined organic layers were washed with brine, dried over Na$_2$SO$_4$, filtered, and concentrated. The residue was purified by HPLC (Zorbax C18, 150 mm×21.2 mm, 18 mL/min, A=0.02% TFA in water, B=MeCN, 10-20% B over 2 min, 20-50% B over 7 min) to provide 1.09 (12 mg, 0.025 mmol, 23%) as a solid. LC-MS (m/z): 476.9 [M+H]$^+$, RT=1.1 min. $^1$H NMR (400 MHz, Chloroform-d) δ 8.39 (dd, J=7.3, 1.0 Hz, 1H), 8.16 (s, 1H), 7.96-7.89 (m, 2H), 7.77 (d, J=2.7 Hz, 1H), 7.64-7.58 (m, 1H), 7.41 (d, J=8.6 Hz, 1H), 7.30 (d, J=8.4 Hz, 2H), 7.12 (dd, J=8.5, 2.8 Hz, 1H), 6.95 (dd, J=7.3, 1.9 Hz, 1H), 6.45 (bs, 1H), 5.62 (bs, 1H), 4.41 (q, J=7.2 Hz, 2H), 3.56 (s, 3H), 1.39 (t, J=7.1 Hz, 3H).

Example 1-10

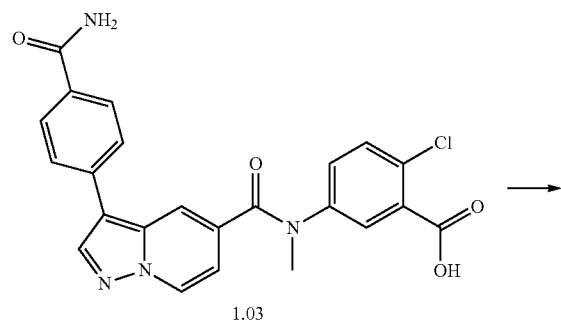

1.03

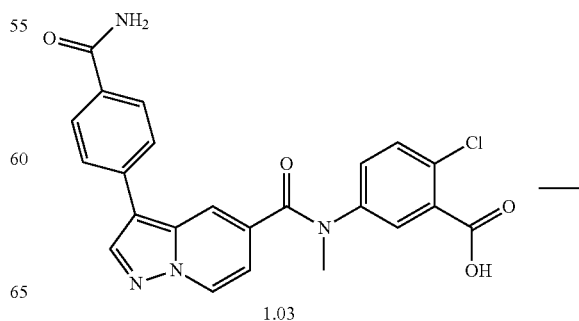

1.03

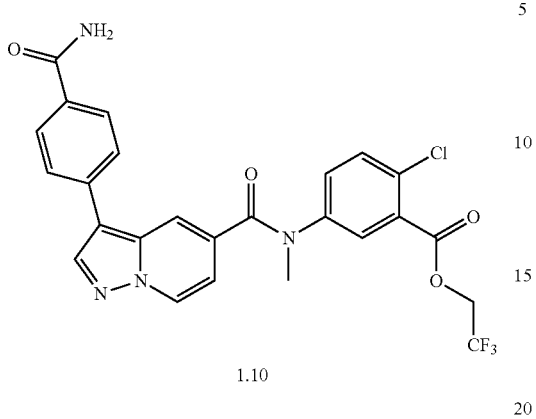

1.10

2,2,2-Trifluoroethyl 5-(3-(4-carbamoylphenyl)-N-methylpyrazolo[1,5-a]pyridine-5-carboxamido)-2-chlorobenzoate (1.10)

A flask was charged with 1.03 (100 mg, 0.222 mmol), DMF (1 mL), DIPEA (0.037 mL), 2,2,2-trifluoroethan-1-ol (7 mg), and HATU (33 mg). The mixture was stirred 12 h, diluted with ice water and extracted with EtOAc. The combined organic layers were washed with brine, dried over $Na_2SO_4$, filtered, and concentrated. The residue was purified by HPLC (Waters Xbridge, 150 mm×21.2 mm, 20 mL/min, A=0.05% TFA in water, B=MeCN, 25-35% B over 2 min, 35-50% B over 6 min) to provide 1.10 (20 mg, 0.037 mmol, 18%) as a solid. LC-MS (m/z): 530.9 [M+H]$^+$, RT=1.394 min. $^1$H NMR (400 MHz, Chloroform-d) δ 8.39 (dd, J=7.2, 0.9 Hz, 1H), 8.18 (s, 1H), 7.92-7.86 (m, 2H), 7.77 (d, J=2.7 Hz, 1H), 7.68 (s, 1H), 7.45 (d, J=8.6 Hz, 1H), 7.42-7.35 (m, 2H), 7.22 (dd, J=8.6, 2.8 Hz, 1H), 6.86 (dd, J=7.3, 1.9 Hz, 1H), 6.39 (bs, 2H), 4.70 (q, J=8.2 Hz, 2H), 3.55 (d, J=1.3 Hz, 3H).

Example 1-11

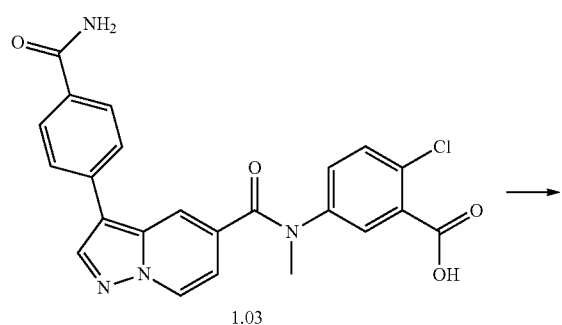

1.03

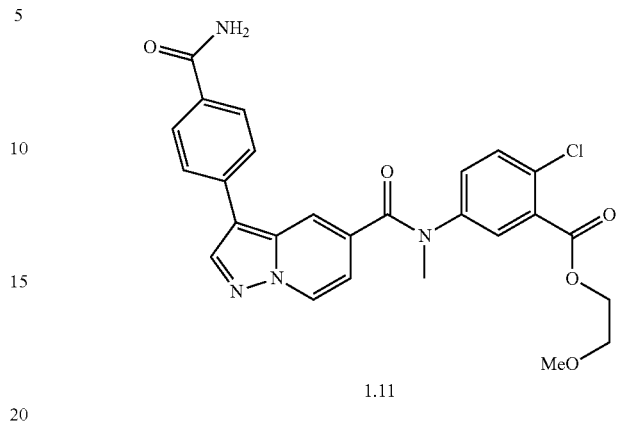

1.11

2-Methoxyethyl 5-(3-(4-carbamoylphenyl)-N-methylpyrazolo[1,5-a]pyridine-5-carboxamido)-2-chlorobenzoate (1.11)

A flask was charged with 1.03 (50 mg, 0.111 mmol), DMF (1 mL), DIPEA (0.10 mL), 2-methoxyethan-1-ol (16 mg), and HATU (84 mg). The mixture was stirred 12 h, diluted with ice water and extracted with EtOAc. The combined organic layers were washed with brine, dried over $Na_2SO_4$, filtered, and concentrated. The residue was purified by HPLC (Zorbax C18, 150 mm×21.2 mm, 18 mL/min, A=0.02% TFA in water, B=MeCN, 20-30% B over 2 min, 30-45% B over 8 min) to provide 1.11 (20 mg, 0.039 mmol, 40%) as a solid. LC-MS (m/z): 506.9 [M+H]$^+$, RT=0.653 min. $^1$H NMR (400 MHz, Chloroform-d) δ 8.41 (d, J=7.3 Hz, 1H), 8.17 (s, 1H), 7.96-7.88 (m, 2H), 7.83 (d, J=2.7 Hz, 1H), 7.57 (d, J=1.5 Hz, 1H), 7.40 (d, J=8.5 Hz, 1H), 7.29 (s, 2H), 7.09 (dd, J=8.6, 2.7 Hz, 1H), 6.99 (dd, J=7.3, 1.9 Hz, 1H), 6.58 (bs, 1H), 5.61 (bs, 1H), 4.62-4.46 (m, 2H), 3.82-3.70 (m, 2H), 3.56 (s, 3H), 3.40 (s, 3H).

Example 1-12

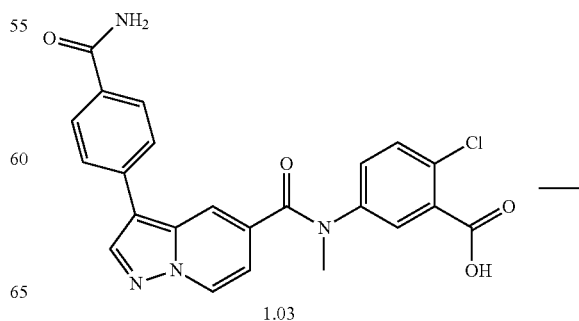

1.03

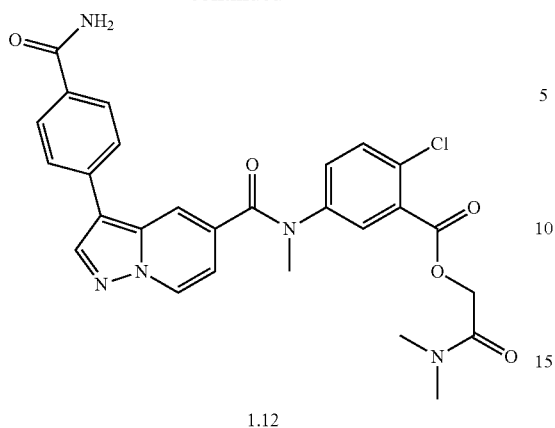

1.12

2-(Dimethylamino)-2-oxoethyl 5-(3-(4-carbamoylphenyl)-N-methylpyrazolo[1,5-a]pyridine-5-carboxamido)-2-chlorobenzoate (1.12)

A flask containing a mixture of 1.03 (100 mg, 0.22 mmol) and DMF (1.5 mL) at 0° C. was charged with K$_2$CO$_3$ (92 mg) and methyl 2-bromo-N,N-diemethylacetamide (74 mg). The mixture was stirred at 80° C. for 2 h. After cooling to rt, the mixture was diluted with ice water and extracted with EtOAc. The combined organic layers were washed with brine, dried over Na$_2$SO$_4$, filtered, and concentrated. The residue was purified by HPLC (Zorbax C18, 150 mm×21.2 mm, 18 mL/min, A=0.02% TFA in water, B=MeCN, 10-20% B over 2 min, 20-50% B over 8 min) to provide 1.12 (16 mg, 0.030 mmol, 14%) as a solid. LC-MS (m/z): 533.9 [M+H]$^+$, RT=0.380 min. $^1$H NMR (400 MHz, Chloroform-d) δ 8.45 (dd, J=7.3, 1.0 Hz, 1H), 8.17 (s, 1H), 8.12 (d, J=2.7 Hz, 1H), 8.01-7.94 (m, 2H), 7.50-7.46 (m, 1H), 7.35 (d, J=8.5 Hz, 1H), 7.23-7.16 (m, 2H), 7.10 (dd, J=7.3, 1.9 Hz, 1H), 7.05-6.97 (m, 1H), 5.03 (s, 2H), 3.57 (s, 3H), 3.09 (s, 3H), 3.02 (s, 3H).

Example 1-13

Isopropyl 5-((t-butoxycarbonyl)amino)-2-chlorobenzoate (1.13a)

To a solution of isopropyl 5-amino-2-chlorobenzoate (1.0 g, 4.7 mmol) in THF (30 mL) and water (7 mL) was added Boc$_2$O (3.1 g) and K$_2$CO$_3$ (1.9 g). The mixture was stirred for 16 h, and then the volatiles were removed under vacuum. The resulting aqueous solution was extracted with EtOAc, dried over Na$_2$SO$_4$, filtered and concentrated. The residue was purified by silica gel chromatography to provide 1.13a (1.4 g, 4.46 mmol, 95% yield). LC-MS (m/z): 331.7.1 [M+NH$_4$]$^+$, RT=0.98 min. $^1$H NMR (400 MHz, Chloroform-d) δ 10.19 (s, 1H), 8.42 (d, J=9.1 Hz, 1H), 7.96 (d, J=2.6 Hz, 1H), 7.44 (dd, J=9.1, 2.6 Hz, 1H), 3.92 (s, 3H), 1.52 (s, 10H).

Isopropyl 5-((t-butoxycarbonyl)(methyl)amino)-2-chlorobenzoate (1.13b)

A flask was charged with 1.13a (1.4 g, 4.5 mmol) and DMF (22 mL) and cooled in an ice bath. 60% NaH (0.25 g) was added portionwise and the mixture stirred for 30 min.

Iodomethane (0.7 mL) was added and the flask was warmed overnight. The mixture was diluted with EtOAc, washed with water, brine, dried over Na₂SO₄, and concentrated to give 1.13b (1.463 g, 4.46 mmol, 100% yield). LC-MS (m/z): 230.1 [M+H]⁺, RT=1.17 min.

Isopropyl 2-chloro-5-(methylamino)benzoate (1.13c)

A vial charged with 1.13b (90 mg, 0.28 mmol) and DCM (212 μL) was cooled in an ice bath. TFA (212 μL) was added and the mixture stirred for 30 min. The volatiles were removed under vacuum and the resulting residue, 1.13c (0.275 mmol, assumed quantitative yield) was used without purification. LC-MS (m/z): 228.2 [M+H]⁺, RT=0.85 min.

Isopropyl 5-(3-bromo-N-methylpyrazolo[1,5-a]pyridine-5-carboxamido)-2-chlorobenzoate (1.13d)

A solution of 3-bromopyrazolo[1,5-a]pyridine-5-carboxylic acid (67 mg, 0.275 mmol) in DCM (0.917 mL) was treated with oxalyl chloride (26 μL) and then DMF (3.19 μL). The resulting solution was allowed to stir for 20 min. NEt₃ (0.096 ml) was added, followed by 1.13c (63 mg) in 1 mL DCM. After 3 h, the mixture was partitioned between EtOAc and water. The layers were separated, and the aqueous layer extracted with EtOAc. The combined organics were dried over Na₂SO₄, filtered, and concentrated to provide 1.13d (0.28 mmol, assumed quantitative) which was used without purification. LC-MS (m/z): 258.1 [M+H]⁺, RT=0.62 min.

Isopropyl 5-(3-(4-carbamoylphenyl)-N-methylpyrazolo[1,5-a]pyridine-5-carboxamido)-2-chlorobenzoate (1.13)

A 5 mL microwave vial was charged with 1.13d (187 mg, 0.415 mmol), (4-carbamoylphenyl)boronic acid (103 mg), PdCl₂(dppf) (61 mg) and K₃PO₄ (264 mg) in dioxane (3.5 mL)/water (0.692 mL). The atmosphere was purged with N₂ for 10 min. The vial was heated in the microwave at 100° C. for 10 min. The mixture was filtered and concentrated. The resulting residue was purified by HPLC (Sunfire Prep C18, 30×100 mm, 60 mL/min, A=0.1% TFA in water, B=MeCN, 30% B for 4 min, 30-70% B over 20 min, 70-95% B over 1 min) to provide 1.13 (7.3 mg, 0.015 mmol, 3.5%) as a solid. LC-MS (m/z): 491.2 [M+H]⁺, RT=0.84 min. ¹H NMR (400 MHz, Chloroform-d) δ 8.69 (d, J=1.8 Hz, 1H), 8.51 (d, J=7.2 Hz, 1H), 8.27 (s, 1H), 8.12 (d, J=8.2 Hz, 2H), 8.02 (s, 1H), 7.84 (dd, J=8.6, 2.1 Hz, 1H), 7.56 (d, J=8.2 Hz, 2H), 7.38 (s, 1H), 6.78 (d, J=7.2 Hz, 1H), 3.96 (s, 3H), 3.64 (s, 3H).

Example 1-14

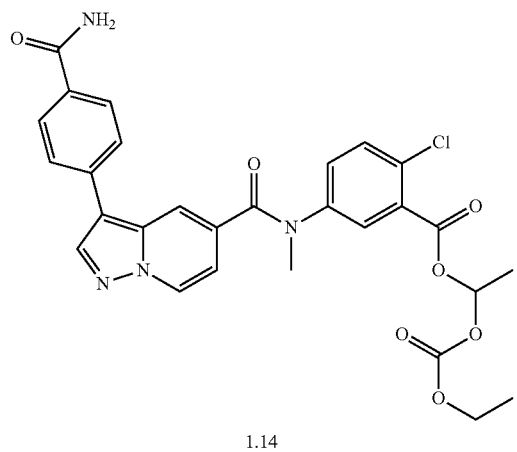

1.14 rac-1-((Ethoxycarbonyl)oxy)ethyl 5-(3-(4-carbamoylphenyl)-N-methylpyrazolo[1,5-a]pyridine-5-carboxamido)-2-chlorobenzoate (1.14)

A flask containing a mixture of 1.03 (50 mg, 0.111 mmol) and DMF (2.0 mL) was charged with K₂CO₃ (30 mg), NaI (2 mg) and 1-chloroethyl ethyl carbonate (35 mg). The mixture was stirred at 80° C. for 2 h. After cooling, the mixture was diluted with ice water and extracted with EtOAc. The combined organic layers were washed with brine, dried over Na₂SO₄, filtered, and concentrated. The residue was purified by HPLC (Kinetex EVO C18, 155 mm×19 mm, 20 mL/min, A=0.1% TFA in water, B=MeCN, 20-40% B over 3 min, 40-70% B over 7 min) to provide 1.14 (13 mg, 0.023 mmol, 20%) as a solid. LC-MS (m/z): 565.3 [M+H]⁺, RT=1.358 min. ¹H NMR (400 MHz, DMSO-d₆) δ 8.63 (d, J=7.2 Hz, 1H), 8.44 (s, 1H), 8.00 (s, 1H), 7.95 (t, J=1.9, 1.9 Hz, 1H), 7.93-7.88 (m, 2H), 7.85 (s, 1H), 7.82-7.77 (m, 1H), 7.69-7.64 (m, 1H), 7.54-7.48 (m, 2H), 7.37 (s, 1H), 6.89-6.84 (m, 1H), 6.80 (q, J=5.4 Hz, 1H), 4.09 (qd, J=7.1, 1.8 Hz, 2H), 3.43 (s, 3H), 1.50 (d, J=5.4 Hz, 3H), 1.15 (t, J=7.1 Hz, 3H).

Example 1-15

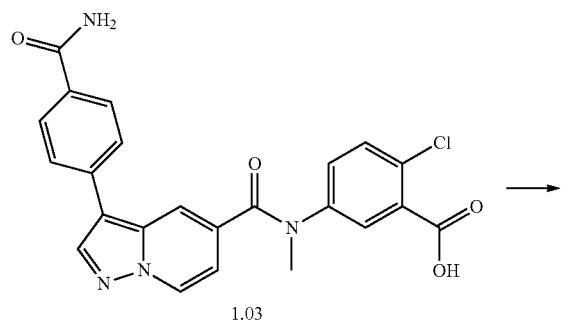

1.03

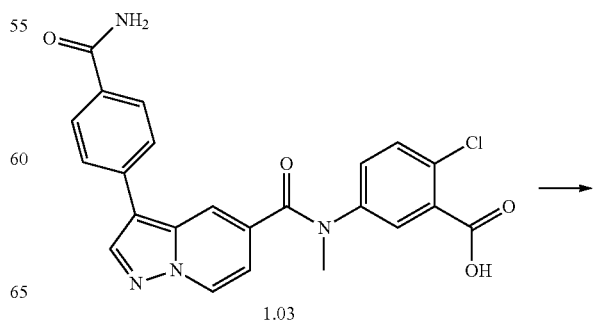

1.03

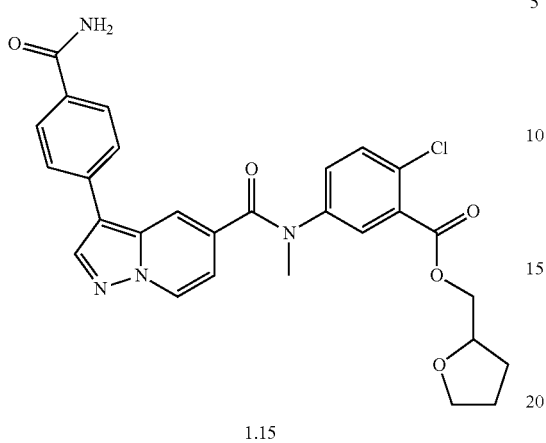

1.15

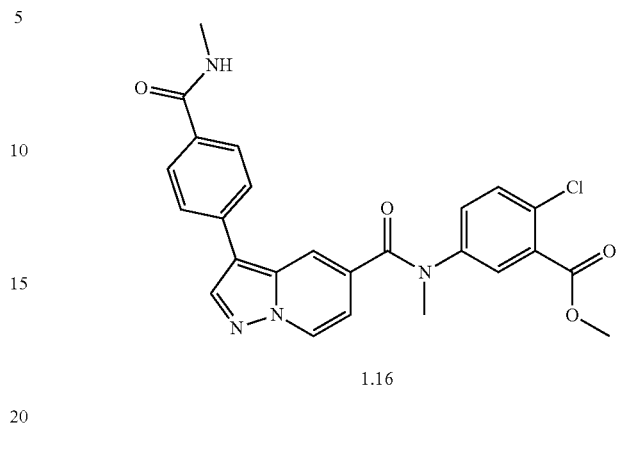

1.16 rac-(Tetrahydrofuran-2-yl)methyl 5-(3-(4-carbamoylphenyl)-N-methylpyrazolo[1,5-a]pyridine-5-carboxamido)-2-chlorobenzoate (1.15)

A flask was charged with 1.03 (50 mg, 0.111 mmol), DMF (1 mL), DIPEA (0.10 mL), (tetrahydrofuran-2-yl)methanol (25 mg), and HATU (84 mg). The mixture was stirred 12 h, diluted with ice water and extracted with EtOAc. The combined organic layers were washed with brine, dried over $Na_2SO_4$, filtered, and concentrated. The residue was purified by HPLC (Zorbax C18, 150 mm×21.2 mm, 20 mL/min, A=0.1% TFA in water, B=MeCN, 30-40% B over 2 min, 40-60% B over 8 min) to provide 1.15 (20 mg, 0.037 mmol, 39%) as a solid. LC-MS (m/z): 533.0 $[M+H]^+$, RT=0.906 min. $^1$H NMR (400 MHz, Chloroform-d) δ 8.43 (dd, J=7.3, 0.9 Hz, 1H), 8.17 (s, 1H), 7.98-7.90 (m, 2H), 7.86 (d, J=2.7 Hz, 1H), 7.53 (t, J=1.4 Hz, 1H), 7.40 (d, J=8.5 Hz, 1H), 7.27 (s, 2H), 7.09 (dd, J=8.5, 2.7 Hz, 1H), 7.03 (dd, J=7.3, 1.9 Hz, 1H), 6.90 (bs, 1H), 6.52 (bs, 1H), 4.47 (dd, J=11.2, 2.8 Hz, 1H), 4.36-4.22 (m, 2H), 3.92-3.77 (m, 2H), 2.22-2.20 (m, 3H), 1.80-1.66 (m, 1H).

Example 1-16

Methyl 2-chloro-5-(N-methyl-3-(4-(methylcarbamoyl)phenyl)pyrazolo[1,5-a]pyridine-5-carboxamido)benzoate (1.16)

To a suspension of compound 1.01d (14.4 g, 34.1 mmol) in THF (360 mL) was added (4-(methylcarbamoyl)phenyl)boronic acid (8.6 g), $Et_3N$ (14.3 mL) and $H_2O$ (67 mL), the mixture was degassed and purged with $N_2$ for three times. $PdCl_2$(dtbpf) (222 mg) was added The mixture was stirred at 53° C. for 3 h. The reaction mixture was diluted with EtOAc and water and filtered. The layers were separated, the organic layer dried over $Na_2SO_4$, filtered, and some of the volatiles removed. The resulting slurry was filtered to collect the solids. The solids were dissolved in EtOH and EtOAc, stirred with Pd-scavaging resing, filtered and fully concentrated. The solid was dissolved in hot EtOAc (150 mL) and slowly cooled. The solids were collected to provide 1.16 (10. g, 21. mmol, 61% yield) as a yellow solid. LC-MS (m/z): 477.0 $[M+H]^+$, RT=0.691 min. $^1$H NMR (400 MHz, Chloroform-d) δ 8.33-8.25 (m, 1H), 8.06 (s, 1H), 7.80-7.75 (m, 2H), 7.71 (d, J=2.80 Hz, 1H), 7.52 (d, J=0.80 Hz, 1H), 7.32 (d, J=8.80 Hz, 1H), 7.24-7.17 (m, 3H), 7.04 (dd, J=2.80, 8.40 Hz, 1H), 6.83 (dd, J=2.00, 7.20 Hz, 1H), 6.39 (br s, 1H), 3.92-3.82 (m, 3H), 3.51-3.40 (m, 3H), 3.00 (d, J=5.20 Hz, 3H).

Example 1-17

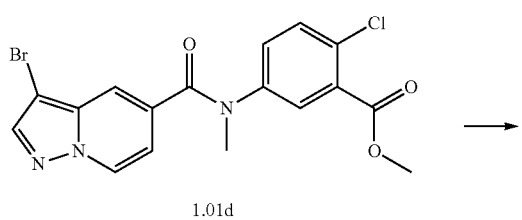

1.01d

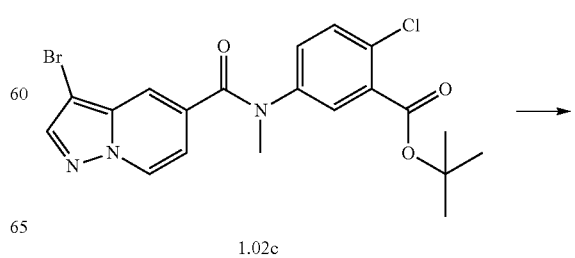

1.02c

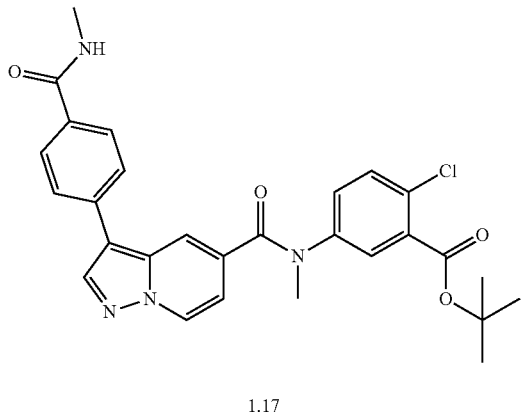

1.17 t-Butyl 2-chloro-5-(N-methyl-3-(4-(methylcarbamoyl)phenyl)pyrazolo[1,5-a]pyrdine-5-carboxamido)benzoate (1.17)

To a solution of (4-(methylcarbamoyl)phenyl)boronic acid (170 mg) and 1.02c (300 mg, 0.645 mmol) in 9:1 dioxane:water (10 mL) was added $Cs_2C_0$(0.628) under argon. $PdCl_2$(dppf) (52 mg) was added. The mixture was stirred at 80° C. for 3 h. The reaction mixture was poured into water and extracted with EtOAc. The combined organics were washed with brine, dried over $Na_2SO_4$, filtered and concentrated. The residue was purified by column chromatography (12 g $SiO_2$, 2-3% MeOH in DCM) to provide compound 1.17 (240 mg, 0.463 mmol, 72% yield) was obtained as a solid. LC-MS (m/z): 519.0 [M+H]$^+$, RT=1.523 min. $^1$H NMR (400 MHz, DMSO-d6) δ 8.68 (d, J=7.2 Hz, 1H), 8.47 (d, J=8.8 Hz, 2H), 7.95-7.87 (m, 3H), 7.70-7.65 (m, 1H), 7.59 (d, J=8.1 Hz, 2H), 7.53 (d, J=1.9 Hz, 2H), 6.88-6.77 (m, 1H), 3.43 (s, 3H), 2.81 (d, J=4.5 Hz, 3H), 1.39 (s, 9H).

Example 1-18

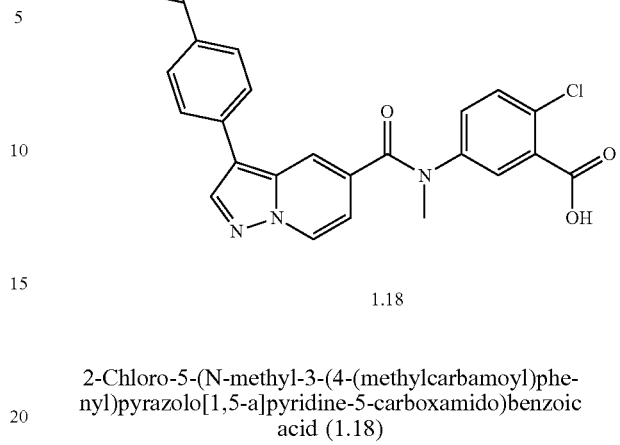

1.18

2-Chloro-5-(N-methyl-3-(4-(methylcarbamoyl)phenyl)pyrazolo[1,5-a]pyridine-5-carboxamido)benzoic acid (1.18)

1.17 (130 mg, 0.25 mmol) was taken up in DCM (5.0 mL). The solution was cooled to 0° C. and TFA (5.0 mL) was added. The mixture was stirred at rt for 6 h and the volatiles were removed in vacuo. The resulting solid was washed with $Et_2O$ and purified by HPLC (Kinetex EVO, 150 mm×21.2 mm, 20 mL/min, A=0.1% TFA in water, B=MeCN, 20-30% B over 2 min, 30-44% B over 7 min) to provide 1.18 (25 mg, 0.055 mmol, 22%) as a solid. LC-MS (m/z): 463.15 [M+H]$^+$, RT=1.41 min. $^1$H NMR (400 MHz, DMSO-d6) δ 8.68 (d, J=7.2 Hz, 1H), 8.52-8.40 (m, 2H), 7.95-7.82 (m, 4H), 7.57 (d, J=8.0 Hz, 2H), 7.49 (d, J=3.2 Hz, 2H), 6.87 (d, J=7.2 Hz, 1H), 3.42 (s, 3H), 2.81 (d, J=4.4 Hz, 3H).

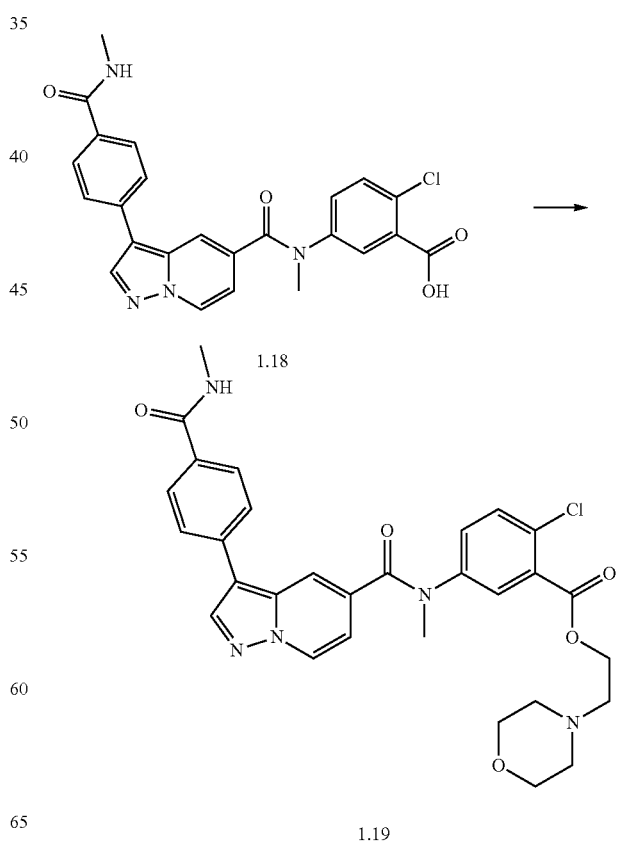

2-Morpholinoethyl 2-chloro-5-(N-methyl-3-(4-(methylcarbamoyl)phenyl)pyrazolo[1,5-a]pyridine-5-carboxamido)benzoate (1.19)

A flask was charged with 1.18 (110 mg, 0.24 mmol), and DMF (2 mL) and cooled to 0 °C. DIPEA (92 mg) and HATU (181 mg) were added. After 20 min, 4-(2-hydroxyethyl)morpholine (94 mg) was added and the mixture warmed to rt over 4 h. The mixture was diluted with ice water and extracted with EtOAc. The combined organic layers were dried over Na$_2$SO$_4$, filtered, and concentrated. The residue was purified by HPLC (Gemini, 150 mm×21.2 mm, 2μ, 18 mL/min, A=0.02% NH$_4$OH in water, B=MeCN, 10-20% B over 2 min, 20-50% B over 7 min) to provide 1.18 (1.4 mg, 0.024 mmol, 11%) as a solid. LC-MS (m/z): 576.3 [M+H]$^+$, RT=1.48 min. $^1$H NMR (400 MHz, Chloroform-d) δ 6 8.68 (d, J=3.6 Hz, 1H), 8.50-8.48 (m, 2H), 7.92-7.88 (m, 2H), 7.79 (s, 1H), 7.58-7.57 (m, 3H), 6.85-6.83 (m, 1H), 4.30 (t, J=5.6 Hz, 2H), 3.48-3.46 (m, 2H), 3.43 (s, 3H), 2.81 (d, J=4.4 Hz, 3H), 2.33-2.32 (m, 4H).

Example 1-20

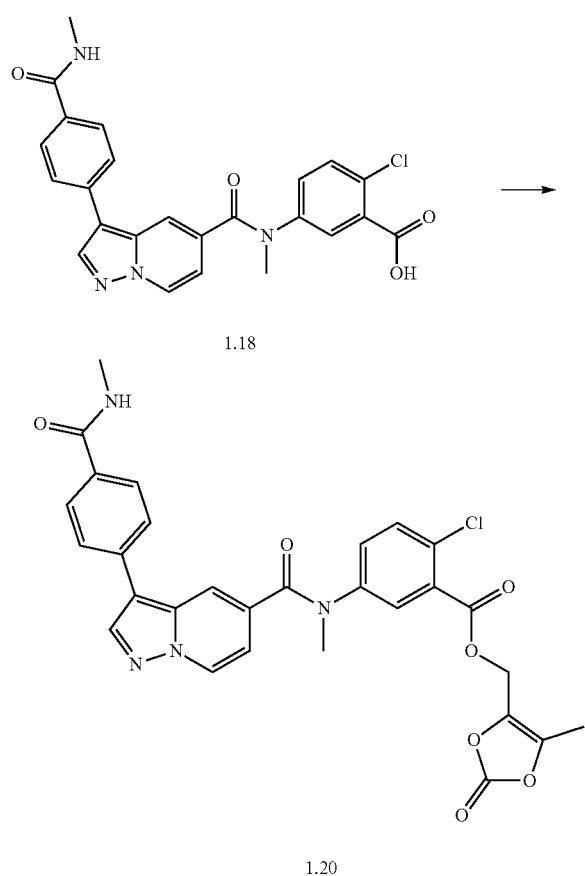

1.18

1.20

(5-Methyl-2-oxo-1,3-dioxol-4-yl)methyl 2-chloro-5-(N-methyl-3-(4-(methylcarbamoyl)phenyl)pyrazolo[1,5-a]pyridine-5-carboxamido)benzoate (1.20)

A flask was charged with 1.18 (100 mg, 0.2 mmol), and DMF (2 mL) and cooled to 0° C. DIPEA (80 mg) and HATU (160 mg) were added. After 20 min, 4-(hydroxymethyl)-5-methyl-1,3-dioxol-2-one (80 mg) was added and the mixture warmed to rt over 16 h. The mixture was diluted with ice water and extracted with EtOAc. The combined organic layers were dried over Na$_2$SO$_4$, filtered, and concentrated. The residue was purified by HPLC (Gemini, 150 mm×21.2 mm, 2μ, 20 mL/min, A=water, B=MeCN, 35-45% B over 2 min, 45-55% B over 6 min) to provide 1.20 (15 mg, 0.002 mmol, 12%) as a solid. LC-MS (m/z): 575.05 [M+H]$^+$, RT=1.47 min.

Example 1.21: Methyl 2-chloro-5-(N-methyl-3-(2-methyl-4-(carbamoyl)phenyl)pyrazolo[1,5-a]pyridine-5-carboxamido)benzoate (1.21)

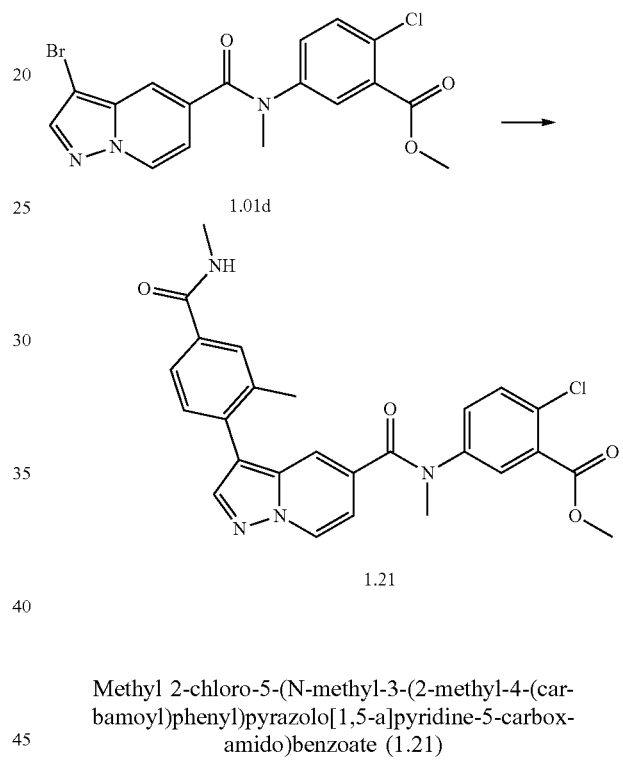

1.01d 1.21

Methyl 2-chloro-5-(N-methyl-3-(2-methyl-4-(carbamoyl)phenyl)pyrazolo[1,5-a]pyridine-5-carboxamido)benzoate (1.21)

To 2 dram vial was added 1.01d (0.025 g, 0.059 mmol) followed by (4-carbamoyl-2-methylphenyl)boronic acid (13 mg), PdCl$_2$(dtbpf) (1.9 mg), 2-MeTHF (0.5 mL), water (0.084 mL), and NEt$_3$ (0.025 mL). The vial was sealed and heated to 65° C. overnight. After cooling, the mixture was partitioned with EtOAc and water. The layers were separated, and the aqueous layer extracted twice with EtOAc. The combined organics were dried over Na$_2$SO$_4$, filtered, and concentrated. The resulting oil was purified by HPLC (Sunfire B-9m-1050, 75 mL/min, 0.1% TFA in water) to provide 1.21 (6.9 mg, 0.1 mmol, 19%) as a yellow solid. LC-MS (m/z): 477.3 [M+H]$^+$, RT=0.75 min. $^1$H NMR (500 MHz, DMSO-d$_6$) δ 8.72 (dd, J=7.2, 0.9 Hz, 1H), 8.23 (s, 1H), 7.98 (s, 1H), 7.84 (dd, J=11.3, 2.3 Hz, 2H), 7.75 (dd, J=7.9, 1.9 Hz, 1H), 7.55 (d, J=8.5 Hz, 1H), 7.47 (dd, J=8.6, 2.7 Hz, 1H), 7.36 (d, J=11.1 Hz, 2H), 7.06 (d, J=7.9 Hz, 1H), 6.93 (dd, J=7.2, 1.9 Hz, 1H), 3.84 (s, 3H), 3.40 (s, 4H), 2.19 (s, 3H).

Example 1.22: Methyl 2-chloro-5-(N-methyl-3-(3-methyl-4-(carbamoyl)phenyl)pyrazolo[1,5-a]pyridine-5-carboxamido)benzoate (1.22)

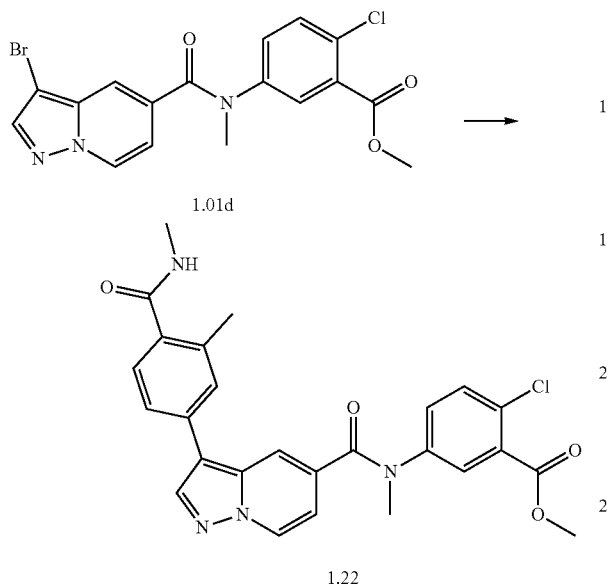

1.01d 1.22

Methyl 2-chloro-5-(N-methyl-3-(3-methyl-4-(carbamoyl)phenyl)pyrazolo[1,5-a]pyridine-5-carboxamido)benzoate (1.22)

To a flask was added 1.01d (80 mg, 0.189 mmol), N-2-dimethyl-4-(4,4,5,5-tetramethyl-1,3,2-dioxaborolan-2-yl)benzamide (62.5 mg), THF (2 mL), water (1 mL), NEt₃ (0.079 mL) and PdCl₂(dtbpf) (24. mg). The mixture was purged with nitrogen, the vial sealed, and then heated to 100° C. for 1 h. The mixture was filtered, concentrated, and purified by HPLC (Sunfire B-9m-1050, 75 mL/min, 0.1% TFA in water) to provide 1.22 (12 mg, 0.019 mmol, 10%) as a solid. HPLC-MS (m/z): 491.1 [M+H]⁺, RT=5.69 min. $^1$H NMR (400 MHz, DMSO-d₆) δ 8.67 (d, J=7.3 Hz, 1H), 8.42 (s, 1H), 8.17 (d, J=4.7 Hz, 1H), 7.92-7.84 (m, 2H), 7.53 (d, J=2.3 Hz, 2H), 7.43-7.33 (m, 2H), 7.33-7.26 (m, 1H), 6.86 (dd, J=7.2, 1.7 Hz, 1H), 3.81 (s, 3H), 2.78 (d, J=4.6 Hz, 3H), 2.41 (s, 3H).

Example 1.23: Methyl 5-(3-(4-carbamoylphenyl)pyrazolo[1,5-a]pyridine-5-carboxamido)-2-chlorobenzoate (1.23)

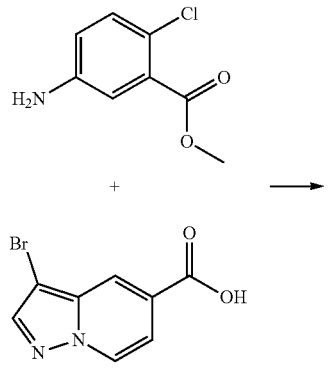

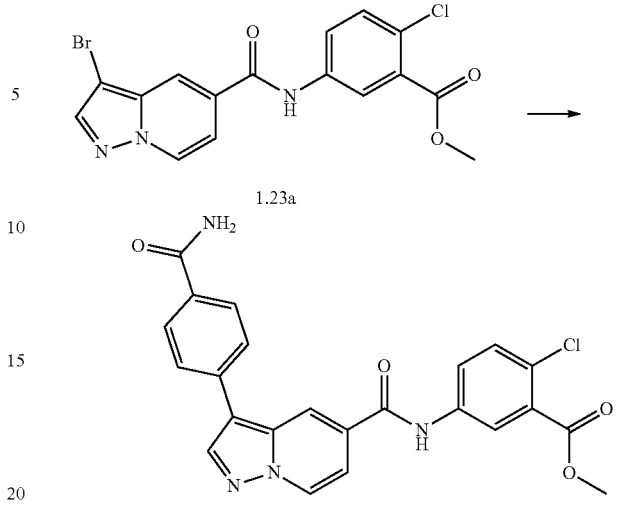

1.23a 1.23

Methyl 5-(3-bromopyrazolo[1,5-a]pyridine-5-carboxamido)-2-chlorobenzoate (1.23a)

To a solution of 3-bromopyrazolo[1,5-a]pyridine-5-carboxylic acid (500 mg, 2.1 mmol) in DCM (8 mL) was added oxalyl chloride (290 mg) followed by DMF (3 drops) dropwise. The mixture was stirred for 1 h and then cooled to 0° C. DIPEA (804 mg) was added followed by methyl 5-amino-2-chlorobenzoate (501 mg) and the mixture was stirred for 30 min. The mixture was concentrated to give a residue. The residue was purified by column chromatography (SiO₂, 0% to 80% Heptane/EtOAc) to provide 1.23a (703 mg, 1.72 mmol, 83% yield). LC-MS (m/z): 408.2 [M+H]⁺, RT=1.06 min. $^1$H NMR (500 MHz, DMSO-d₆) δ 10.82 (s, 1H), 8.89 (d, J=7.1 Hz, 1H), 8.37-8.31 (m, 3H), 8.07-8.01 (m, 1H), 7.62 (d, J=9.0 Hz, 1H), 7.46 (d, J=7.2 Hz, 1H), 3.91 (d, J=4.5 Hz, 3H).

Methyl 5-(3-(4-carbamoylphenyl)pyrazolo[1,5-a]pyridine-5-carboxamido)-2-chlorobenzoate (1.23)

A vial was charged with 1.23a (50 mg, 0.122 mmol), (4-carbamoylphenyl)boronic acid (28 mg), PdCl₂(dtbpf) (8 mg) and NEt₃ (37 mg) in THF (0.82 ml)/Water (0.41 ml). The atmosphere was purged with N₂. The vial was heated at 65° C. for 15 min. The mixture was cooled, and the solids washed with EtOAc, followed by dissolution in DMF and filtering through diatomaceous earth. The solution was diluted with EtOAc, washed twice with brine, dried over MgSO₄, filtered and concentrated. The residue was purified by HPLC (Sunfire B-9m-3070, 75 mL/min, 0.1% TFA in water) to yield 1.23 (2.7 mg, 0.047 mmol, 4%) as a solid. LC-MS (m/z): 449.3 [M+H]+, RT=0.81 min. $^1$H NMR (500 MHz, DMSO-d₆) δ 10.82 (s, 1H), 8.92 (d, J=7.2 Hz, 1H), 8.67 (d, J=1.5 Hz, 1H), 8.62 (s, 1H), 8.33 (d, J=2.7 Hz, 1H), 8.09-8.02 (m, 3H), 7.91 (d, J=8.3 Hz, 2H), 7.63 (d, J=8.7 Hz, 1H), 7.46 (dd, J=7.2, 1.9 Hz, 1H), 7.40 (s, 1H), 3.91 (s, 3H), 3.31 (s, 1H), 2.56 (s, 1H).

Example 1.24: Methyl 2-chloro-5-(3-(4-(methylcarbamoyl)phenyl)pyrazolo[1,5-a]pyridine-5-carboxamido)benzoate

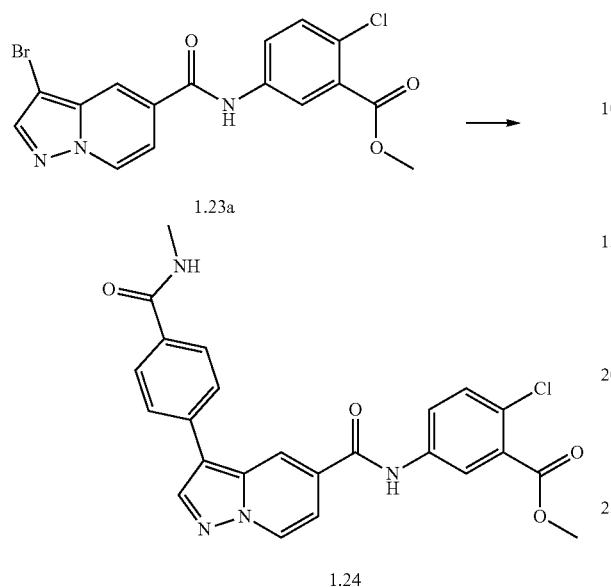

1.23a 1.24

Methyl 2-chloro-5-(3-(4-(methylcarbamoyl)phenyl)pyrazolo[1,5-a]pyrdine-5-carboxamido)benzoate (1.24)

A vial was charged with 1.23a (50 mg, 0.122 mmol), P(t-Bu)$_3$Pd G2 (1.567 mg), and (4-(methylcarbamoyl)phenyl)boronic acid (35.1 mg) under inert atmosphere. t-Amyl alcohol (1 mL), water (173 µl), and NEt$_3$ (51.2 µl) were added. The mixture was heated to 60° C. for 1 h and then concentrated. The residue was purified by HPLC (Sunfire B-9m-2060, 75 mL/min, 0.1% TFA in water) to yield 1.24 (16.5 mg, 0.028 mmol, 23%) as a solid. LC-MS (m/z): 463.3 [M+H]$^+$, RT=0.83 min. $^1$H NMR (400 MHz, DMSO-d$_6$) δ 10.80 (s, 1H), 8.91 (dd, J=7.3, 0.9 Hz, 1H), 8.65 (dd, J=2.0, 1.0 Hz, 1H), 8.60 (s, 1H), 8.48 (d, J=4.8 Hz, 1H), 8.32 (d, J=2.6 Hz, 1H), 8.05 (dd, J=8.8, 2.7 Hz, 1H), 8.02-7.96 (m, 2H), 7.94-7.87 (m, 2H), 7.62 (d, J=8.8 Hz, 1H), 7.45 (dd, J=7.3, 1.9 Hz, 1H), 3.90 (s, 3H), 2.83 (d, J=4.5 Hz, 3H).

Example 1.25: Methyl 5-(3-(4-carbamoylphenyl)-N-methylpyrazolo[1,5-a]pyridine-5-carboxamido)-2-(trifluoromethoxy)benzoate (1.25)

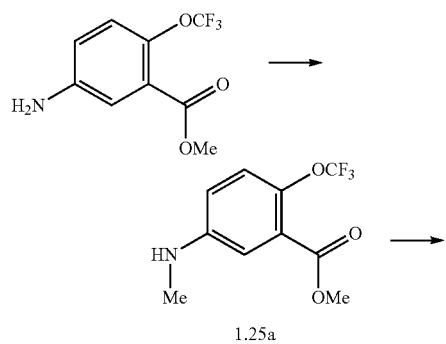

1.25a

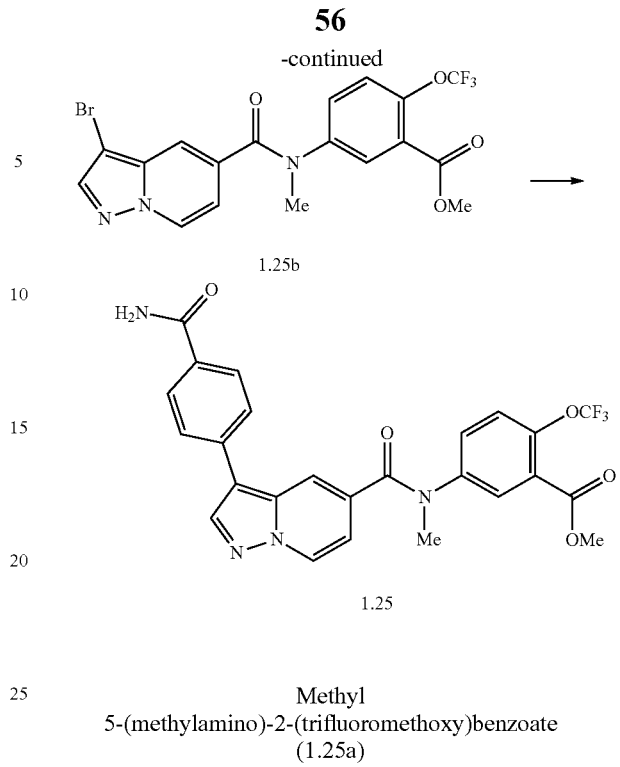

1.25b 1.25

Methyl 5-(methylamino)-2-(trifluoromethoxy)benzoate (1.25a)

Methyl 5-amino-2-(trifluoromethoxy)benzoate (500 mg, 2.1 mmol) was dissolved in DMF (5 mL) in an oven dried vial and cooled to 0° C. 60% NaH in oil (100 mg) was added in single portion. After 10 min, iodomethane (360 mg) was added dropwise and the reaction warmed to room temperature. After 2 h, the mixture was diluted with EtOAc and NH$_4$Cl (sat aq). The layers were separated, and the aqueous layer extracted once with EtOAc. The combined organics were dried over MgSO$_4$, filtered, concentrated. The resulting residue was purified by column chromatography (SiO$_2$, 0% to 60% Heptane/EtOAc) to provide 1.25a (85 mg, 0.34 mmol, 16%). LC-MS (m/z): 250.3 [M+H]$^+$, RT=0.97 min.

Methyl 5-(3-bromo-N-methylpyrazolo[1,5-a]pyridine-5-carboxamido)-2-(trifluoromethoxy)benzoate (1.25b)

To a solution of 3-bromopyrazolo[1,5-a]pyridine-5-carboxylic acid (82 mg, 0.341 mmol) in DCM (3 mL) was added oxalyl chloride (45 mg) followed by DMF (1 drop) dropwise. The mixture was stirred for 1 h and then cooled to 0° C. DIPEA (132 mg) was added followed by 1.25a (85 mg) and the mixture was stirred for 30 min and concentrated to give a residue. The residue was purified by column chromatography (SiO$_2$, 0% to 100% Heptane/EtOAc) to provide 1.25b (130 mg, 0.28 mmol, 83% yield). LC-MS (m/z): 350.3 [M+H]$^+$, RT=1.06 min. $^1$H NMR (500 MHz, Chloroform-d) δ 8.25 (d, J=7.3 Hz, 1H), 7.95 (d, J=2.4 Hz, 1H), 7.83 (d, J=2.8 Hz, 1H), 7.59 (s, 1H), 7.28 (q, J=8.8, 7.7 Hz, 3H), 6.67 (d, J=7.2 Hz, 1H), 3.94 (d, J=2.4 Hz, 3H), 3.56 (d, J=2.5 Hz, 3H).

Methyl 5-(3-(4-carbamoylphenyl)-N-methylpyrazolo[1,5-a]pyridine-5-carboxamido)-2-(trifluoromethoxy)benzoate (1.25)

A vial was charged with 1.25b (65 mg, 0.138 mmol), (4-carbamoylphenyl)boronic acid (39 mg), PdCl$_2$(dtbpf) (9 mg) and NEt$_3$ (42 mg) in THF (0.9 ml)/Water (0.45 ml). The atmosphere was purged with N$_2$. The vial was heated at 60° C. for 25 min. The mixture was dilute with water and extracted 3× with EtOAc. The combined organics were filtered and concentrated The residue was purified by HPLC (Sunfire B-9m-1050, 75 mL/min, 0.1% TFA in water) to yield 1.25 (42 mg, 0.066 mmol, 48%) as a solid. LC-MS (m/z): 513.3 [M+H]$^+$, RT=0.95 min. $^1$H NMR (500 MHz, DMSO-d$_6$) δ 8.70 (d, J=7.2 Hz, 1H), 8.48 (s, 1H), 8.04 (d, J=2.8 Hz, 1H), 8.00 (s, 1H), 7.97-7.92 (m, 2H), 7.88 (s, 1H), 7.67 (dd, J=8.8, 2.8 Hz, 1H), 7.55 (d, J=8.0 Hz, 2H), 7.48 (d, J=8.7 Hz, 1H), 7.36 (s, 1H), 6.92 (d, J=7.1 Hz, 1H), 3.84 (s, 3H), 3.45 (s, 3H).

Example 1.26: Methyl 5-(N-methyl-3-(4-(methylcarbamoyl)phenyl)pyrazolo[1,5-a]pyridine-5-carboxamido)-2-(trifluoromethoxy)benzoate (1.26)

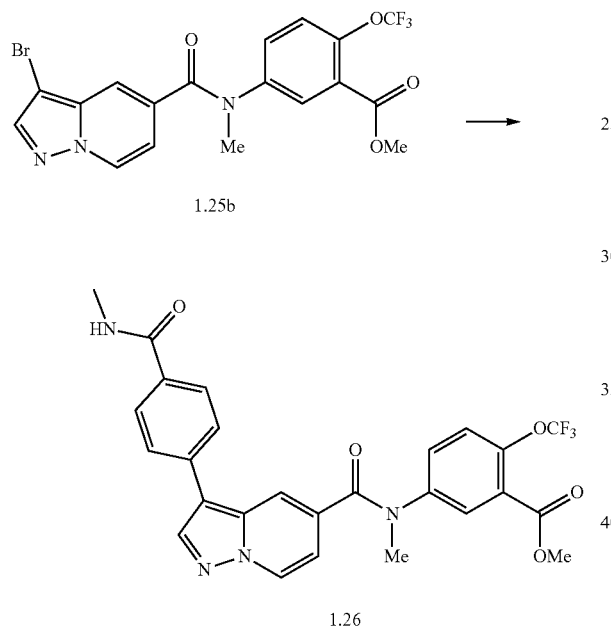

Methyl 5-(N-methyl-3-(4-(methylcarbamoyl)phenyl)pyrazolo[1,5-a]pyridine-5-carboxamido)-2-(trifluoromethoxy)benzoate (1.26)

A vial was charged with 1.25b (65 mg, 0.138 mmol), (4-(methylcarbamoyl)phenyl)boronic acid (42 mg), PdCl$_2$(dtbpf) (9 mg) and NEt$_3$ (42 mg) in THF (0.9 ml)/Water (0.45 ml). The atmosphere was purged with N$_2$. The vial was heated at 60° C. for 25 min. The mixture was dilute with water and extracted 3× with EtOAc. The combined organics were filtered and concentrated The residue was purified by HPLC (Sunfire B-9m-2060, 75 mL/min, 0.1% TFA in water) to yield 1.26 (48 mg, 0.075 mmol, 55%) as a solid. LC-MS (m/z): 527.3 [M+H]$^+$, RT=0.99 min. $^1$H NMR (400 MHz, DMSO-d$_6$) δ8.70 (dd, J=7.2, 0.9 Hz, 1H), 8.46 (d, J=12.4 Hz, 2H), 8.04 (d, J=2.7 Hz, 1H), 7.90 (dd, J=10.3, 3.6 Hz, 3H), 7.66 (dd, J=8.8, 2.8 Hz, 1H), 7.55 (d, J=8.1 Hz, 2H), 7.48 (d, J=8.7 Hz, 1H), 6.92 (dd, J=7.2, 1.8 Hz, 1H), 3.85 (s, 4H), 3.45 (s, 3H), 2.82 (d, J=4.4 Hz, 3H).

Example 1.27: Methyl 5-(3-(4-carbamoylphenyl)-N-methylpyrazolo[1,5-a]pyridine-5-carboxamido)-2-cyanobenzoate (1.27)

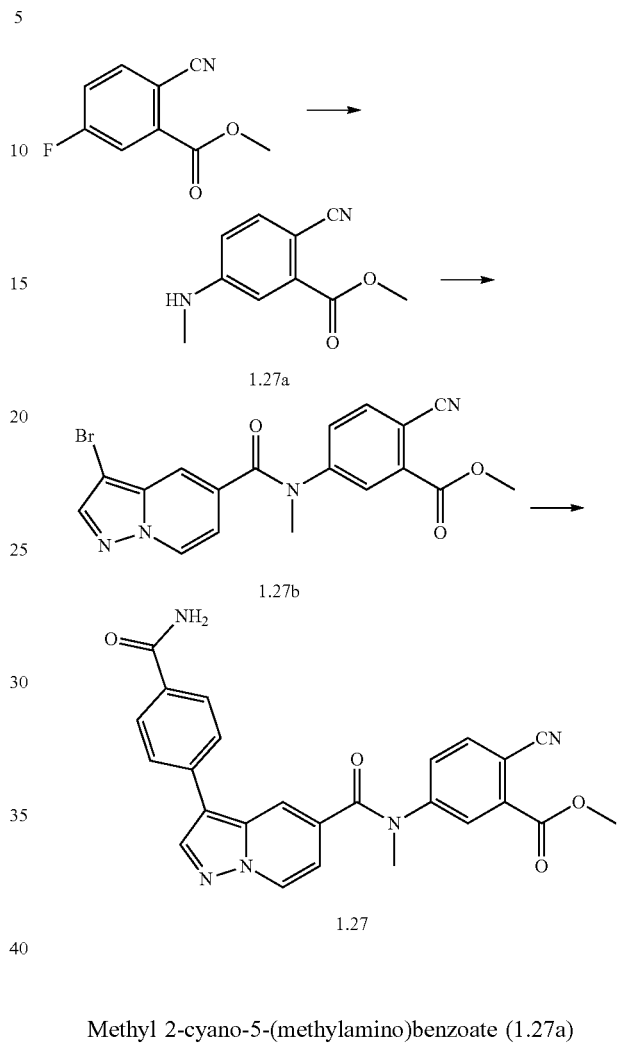

Methyl 2-cyano-5-(methylamino)benzoate (1.27a)

A microwave vial was charged with methyl 2-cyano-5-fluorobenzoate (200 mg, 1.1 mmol), 2.0 M methylamine in THF (1.7 mL) and DMA (1.1 mL). The mixture was stirred for 30 min at 130° C. in a microwave. The volatiles were removed and the residue purified by column chromatography to provide 1.27a (160 mg, 0.84 mmol, 75%). LC-MS (m/z): 191.1 [M+H]$^+$, RT=0.65 min.

Methyl 5-(3-bromo-N-methylpyrazolo[1,5-a]pyridine-5-carboxamido)-2-cyanobenzoate (1.27b)

A solution of 3-bromopyrazolo[1,5-a]pyridine-5-carboxylic acid (60 mg, 0.25 mmol) in DCM (2.5 mL) was treated with oxalyl chloride (95 mg) and one drop of DMF. The resulting solution was allowed to stir at rt for one hour, then was concentrated and dried briefly under high vacuum. The residue was dissolved in DCM (2.5 mL). DIPEA (0.131 mL) and 1.27a (65 mg) were added. The mixture was stirred for 3 hr and concentrated under reduced pressure. The residue was purified by silica gel chromatography to provide 1.27b (62 mg, 0.150 mmol, 60% yield). LC-MS (m/z): 413.0 [M+H]$^+$, RT=0.83 min.

Methyl 5-(3-(4-carbamoylphenyl)-N-methylpyrazolo[1,5-a]pyridine-5-carboxamido)-2-cyanobenzoate (1.27)

A microwave vial was charged with 1.27b (62.0 mg, 0.15 mmol), (4-carbamoylphenyl)boronic acid (37 mg), PdCl$_2$(dppf) (22 mg) and K$_3$PO$_4$ (96 mg), dioxane (1.2 mL) and water (250 µl). The vial was sealed, purged with N$_2$ for 10 min, and then placed in a microwave 100° C. for 20 min. The mixture was filtered, and concentrated. The residue was purified by HPLC (Sunfire B-9m-1050, 75 mL/min, 0.1% TFA in water) to yield 1.27 (27 mg, 0.06 mmol, 40%) as a solid. LC-MS (m/z): 454.5 [M+H]$^+$, RT=0.68 min. $^1$H NMR (400 MHz, Chloroform-d) δ 8.37 (dd, J=7.3, 0.9 Hz, 1H), 8.18 (s, 1H), 8.03 (d, J=2.3 Hz, 1H), 7.92-7.84 (m, 2H), 7.75-7.68 (m, 2H), 7.43-7.30 (m, 3H), 6.79 (dd, J=7.3, 1.9 Hz, 1H), 6.24 (s, 1H), 5.74 (s, 1H), 4.01 (s, 3H), 3.59 (s, 3H).

Example 2.1: Methyl 2-chloro-5-(N-methyl-3-(4-(methylcarbamoyl)phenyl)imidazo[1,2-a]pyrazine-6-carboxamido)benzoate

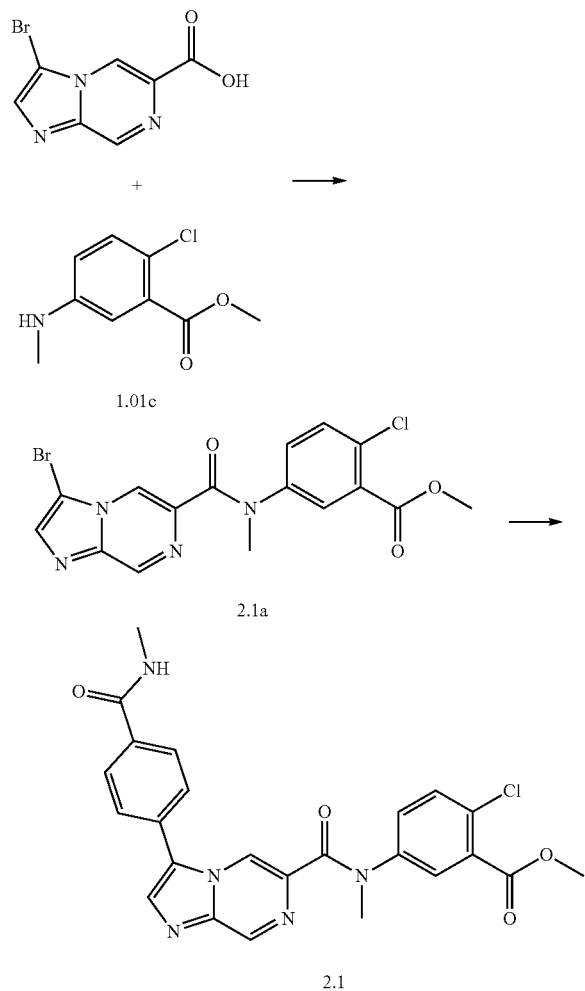

Methyl 5-(3-bromo-N-methylimidazo[1,2-a]pyrazine-6-carboxamido)-2-chlorobenzoate (2.1a)

A flask was charged with 3-bromoimidazo[1,2-a]pyrazine-6-carboxylic acid (300 mg, 1.24 mmol), 1.01c (240 mg), and pyridine (10 mL). The flask was cooled to 0° C. and POCl$_3$ (570 mg) was added slowly. The ice bath was removed. At 30 min, the mixture was poured into ice water and the aqueous layer extracted with DCM. The combined organics were washed with brine, dried over Na$_2$SO$_4$, filtered and concentrated to provide 2.1a (400 mg, 0.94 mmol, 76%) that was sufficiently clean to use in the next reaction. LC-MS (m/z): 425.0 [M+3]$^+$, RT=0.87 min.

Methyl 2-chloro-5-(N-methyl-3-(4-(methylcarbamoyl)phenyl)imidazo[1,2-a]pyrazine-6-carboxamido)benzoate (2.1)

A sealed tube was charged with 2.1a (200 mg, 0.472 mmol), (4-(methylcarbamoyl)phenyl)boronic acid (84 mg), dioxane (4 mL), and water (1 mL). CsF (143 mg) was added, followed by Pd(amphos)Cl$_2$ (16 mg). The mixture was heated at 90° C. for 1.5 h. The reaction mixture was cooled, quenched with water and extracted with ethyl acetate. The combined organic layers were washed with brine, dried over Na$_2$SO$_4$, filtered, and concentrated under reduced pressure. The residue was purified by HPLC (LUNA Phenomenex, 250 mm×21.2 mm, 20 mL/min, A=0.02% TFA in water, B=MeCN, 20-30% B over 2 min, 30-60% B over 6 min) to provide 2.1 (40 mg, 0.083 mmol, 17%) as a solid. LC-MS (m/z): 478.1 [M+1]$^+$, RT=0.52 min. $^1$H NMR (300 MHz, DMSO-d$_6$) δ8.88 (s, 2H), 8.69-8.50 (m, 1H), 8.21 (s, 1H), 8.05 (d, J=7.9 Hz, 2H), 7.89-7.72 (m, 3H), 7.45 (s, 2H), 3.80 (s, 3H), 3.44 (s, 3H), 2.84 (d, J=4.9 Hz, 3H).

Example 3.1: Methyl 2-chloro-5-(N-methyl-3-(4-(methylcarbamoyl)phenyl)pyrazolo[1,5-c]pyrimidine-5-carboxamido)benzoate

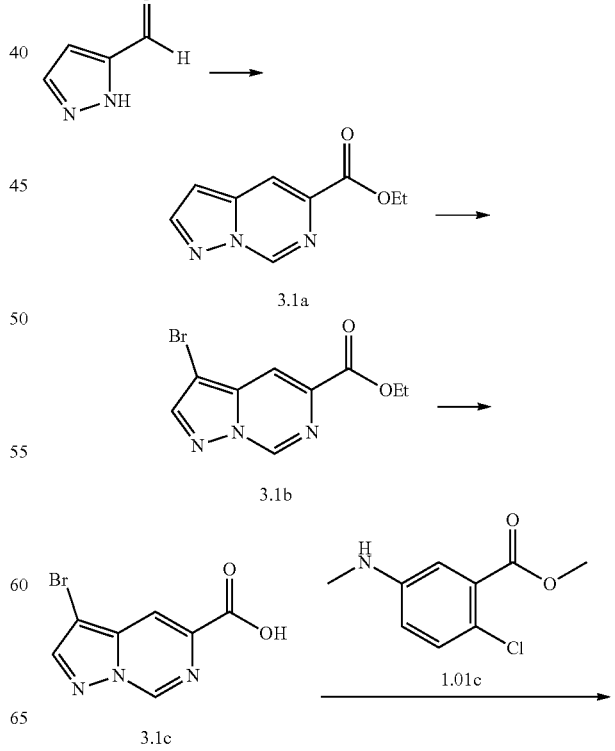

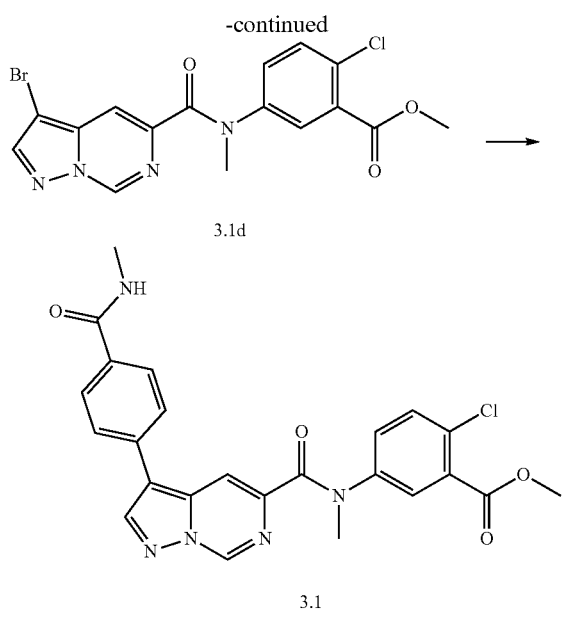

Ethyl pyrazolo[1,5-c]pyrimidine-5-carboxylate (3.1a)

1H-Pyrazole-5-carbaldehyde (14.4 g, 150 mmol) was taken up in THF (150 mL). DBU (5.71 g) and ethyl 2-isocyanoacetate (17 g) were added. The mixture was heated at 55° C. overnight, then cooled to rt and the volatiles were removed. The crude material was purified by flash column chromatography (0 to 100% EtOAc in heptane) to provide 3.1a (13.5 g, 70.6 mmol, 47%). LC-MS (m/z): 192.2 [M+H]$^+$, RT=0.49 min. $^1$H NMR (500 MHz, Chloroform-d) δ 9.33 (s, 1H), 8.38 (s, 1H), 8.19 (s, 1H), 6.80 (s, 1H), 4.49 (q, J=7.5 Hz, 2H), 1.46 (t, J=7.2 Hz, 2H).

Ethyl 3-bromopyrazolo[1,5-c]pyrimidine-5-carboxylate (3.1b)

3.1a (6.8 g, 36 mmol) was dissolved in DCM (178 mL). NBS (8.2 g) was added. After 2 h of stirring, additional NBS (4 g) was added. After 2 h, the reaction was quenched with saturated aq. thiosulfate. The layers were separated and the organic layer was washed with saturated aq. bicarbonate, dried over Na$_2$SO$_4$, filtered, and concentrated to provide 3.1b (9.5 g, 35 mmol, 98%). LC-MS (m/z): 272.1 [M+H]$^+$, RT=0.67 min. $^1$H NMR (400 MHz, Chloroform-d) δ 9.25 (d, J=1.4 Hz, 1H), 8.32 (d, J=1.4 Hz, 1H), 8.15 (s, 1H), 4.50 (q, J=7.1 Hz, 3H), 1.46 (t, J=7.1 Hz, 4H).

3-Bromopyrazolo[1,5-c]pyrimidine-5-carboxylic acid (3.1c)

3.1b (9.45 g, 35.0 mmol) was dissolved in methanol (175 mL). 2.0 M NaOH (87 mL) was added slowly and the mixture stirred for 45 min. The reaction was acidified to a pH of ~2 with 10% aq. HCl and then partitioned with EtOAc. The mixture was filtered through a Buechener funnel to collect the precipitate. The filtrate was separated and the organic layer concentrated. The combined solids were dried in a vacuum oven to provide 3.1c (7.26 g, 30.0 mmol, 86%). LC-MS (m/z): 242.1 [M+H]$^+$, RT=0.47 min. $^1$H NMR (500 MHz, DMSO-d6) δ 9.62 (d, J=1.4 Hz, 1H), 8.53 (s, 1H), 8.15 (d, J=1.4 Hz, 1H).

Methyl 5-(3-bromo-N-methylpyrazolo[1,5-c]pyrimidine-5-carboxamido)-2-chlorobenzoate (3.1d)

A solution of 3.1c (632 mg, 2.61 mmol) in DCM (2.6 mL) was treated with oxalyl chloride (251 µl) and DMF (10 µl, 0.131 mmol). The resulting solution was allowed to stir 30 min. NEt$_3$ (909 µL) was added, followed by 1.01c (616 mg) in 1 mL DCM. The mixture was stirred for 3 h, and then partitioned with water and EtOAc. The aqueous layer was extracted with EtOAc. The combined organics were dried over Na$_2$SO$_4$, filtered, concentrated, and purified by flash column chromatography to provide 3.1a (630 mg, 1.5 mmol, 57.0% yield) which was used in following step without further purification. LC-MS (m/z): 423.2 [M+1]$^+$, RT=0.88 min.

Methyl 2-chloro-5-(N-methyl-3-(4-(methylcarbamoyl)phenyl)pyrazolo[1,5-c]pyrimidine-5-carboxamido)benzoate (3.1)

A vial was charged with (4-(methylcarbamoyl)phenyl) boronic acid (202 mg), 3.1d (342 mg, 0.807 mmol), THF (8.5 mL), water (1.6 mL) and NEt$_3$ (338 µl) and the purged with N$_2$. PdCl$_2$(dtbpf) (10.52 mg) was added. The mixture was stirred at 53° C. for 8 h. Additional (4-(methylcarbamoyl)phenyl)boronic acid (100 mg) and PdCl$_2$(dtbpf) (30 mg) were added and the mixture heated for another 10 min. The mixture was diluted with EtOAc, washed with water, brine, and concentrated. The residue was purified by flash column chromatography then by HPLC (Amino column C3_20-25, CO$_2$/MeOH, 80 mL/min) to give 3.1 (230 mg, 0.476 mmol, 59.0% yield) as a solid. LC-MS (m/z): 478.4 [M+1]$^+$, RT=0.86 min. $^1$H NMR (500 MHz, DMSO-d$_6$) δ 9.43 (s, 1H), 8.79 (s, 1H), 8.52 (q, J=4.4 Hz, 1H), 8.31 (d, J=1.5 Hz, 1H), 8.00-7.94 (m, 2H), 7.86-7.79 (m, 3H), 7.50 (d, J=10.8 Hz, 2H), 3.80 (s, 3H), 3.46 (s, 3H), 2.84 (d, J=4.5 Hz, 3H).

Example 4.1: Methyl 2-(3-(4-carbamoylphenyl)-N-methylpyrazolo[1,5-a]pyridine-5-carboxamido)-5-chlorobenzoate (4.1)

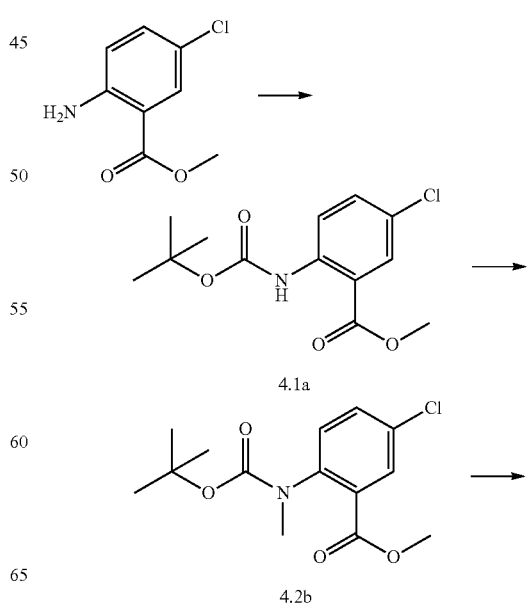

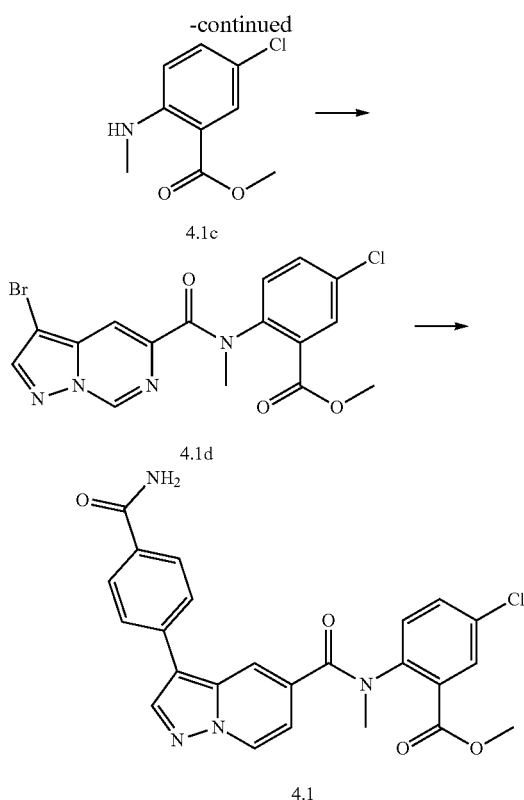

Methyl 2-((tert-butoxycarbonyl)amino)-5-chlorobenzoate (4.1a)

Methyl 2-amino-5-chlorobenzoate (2.0 g, 11 mmol) was taken up in DCM (72 mL). Boc₂O (3.53 g) and DMAP (0.1 g) were added sequentially. The mixture was stirred overnight, concentrated and purified by flash column chromatography to give 4.1a (1.2 g, 4.3 mmol, 40% yield). LC-MS (m/z): 186.1 [M+H]⁺, RT=1.11 min. ¹H NMR (400 MHz, Chloroform-d) δ 10.19 (s, 1H), 8.42 (d, J=9.1 Hz, 1H), 7.96 (d, J=2.6 Hz, 1H), 7.44 (dd, J=9.1, 2.6 Hz, 1H), 3.92 (s, 3H), 1.52 (s, 10H).

Methyl 2-((tert-butoxycarbonyl)(methyl)amino)-5-chlorobenzoate (4.1b)

4.1a (1.2 g, 4.2 mmol) was taken up in DMF (28.0 ml) and the flask was cooled in an ice bath. 60% NaH (0.25 g) was added. After stirring 30 min, iodomethane (0.39 mL) was added and the flask was allowed to warm to rt overnight. The mixture was diluted with EtOAc, washed with water, brine, dried over Na₂SO₄, and concentrated to give 4.1b (1.3 g, 4.2 mmol, 99% yield). LC-MS (m/z): 200.1 [M+H-(t-BuO₂C)]⁺, RT=0.92 min.

Methyl 5-chloro-2-(methylamino)benzoate (4.1c)

4.1b (1.2 g, 4.0 mmol) was taken up DCM (4.0 mL) and the flask cooled in an ice bath. TFA (3.1 mL) was added. After 30 min, the volatiles were removed under vacuum to provide 4.1c (0.80 g, 4.0 mmol, 100%) as a TFA salt, which was used without purification. LC-MS (m/z): 200.1 [M+H]⁺, RT=0.86 min.

Methyl 2-(3-bromo-N-methylpyrazolo[1,5-a]pyridine-5-carboxamido)-5-chlorobenzoate (4.1d)

A solution of 3-bromopyrazolo[1,5-a]pyridine-5-carboxylic acid (0.96 g, 4.0 mmol) in DCM (40.0 mL) was treated with oxalyl chloride (1.5 g) and several drops of DMF. The resulting solution was allowed to stir for 1 h, then was concentrated and dried briefly under high vacuum. The resulting acid chloride was diluted with DCM (40 mL), and to this solution was added 4.1c (0.80 g) and DIPEA (2.6 g). The resulting mixture was stirred 12 h. The solvent was removed under reduced pressure, and the residue was purified by silica gel chromatography to provide 4.1d (1.2 g, 2.8 mmol, 71%). LC-MS (m/z): 422.1 [M+1]⁺, RT=0.87 min.

Methyl 2-(3-(4-carbamoylphenyl)-N-methylpyrazolo[1,5-a]pyridine-5-carboxamido)-5-chlorobenzoate (4.1)

4.1d (0.79 g, 1.9 mmol), (4-carbamoylphenyl)boronic acid (0.46 g), PdCl₂(dtbpf) (0.27 g) and K₃PO₄ (1.2 g) were taken up in dioxane (15 mL) and water (3.1 mL) in a microwave vial. The vial was purged with N₂ for 10 min and then heated in a microwave at 100° C. for 10 min. The mixture was filtered, concentrated, and purified by HPLC (Amino column C3_20-25, CO₂/MeOH, 80 mL/min) to yield 4.1 (650 mg, 1.4 mmol, 75% yield) as a yellow solid. LC-MS (m/z): 463.2 [M+1]⁺, RT=0.76 min. ¹H NMR (400 MHz, Chloroform-d) δ 8.69 (d, J=1.8 Hz, 1H), 8.51 (d, J=7.2 Hz, 1H), 8.27 (s, 1H), 8.12 (d, J=8.2 Hz, 2H), 8.02 (s, 1H), 7.84 (dd, J=8.6, 2.1 Hz, 1H), 7.56 (d, J=8.2 Hz, 2H), 7.38 (s, 1H), 6.78 (d, J=7.2 Hz, 1H), 3.96 (s, 3H), 3.64 (s, 3H).

Biological Assays

The activity of a compound used in the method of the present invention for inhibition of parasitemai in host cells can be assessed by the following assays. It is understood that the assays illustrate the invention without in any way limiting the scope of the invention.

Culturing and Maintaining Host Cells and *Cryptosporidium* Parasite

Human ileocecal colorectal adenocarcinoma cells (HCT-8 [HRT-18] ATCC, CCL-34) were maintained in T-175 flasks (Corning, 431080) in complete growth medium (RPMI-1640 medium (Gibco, 11875) supplemented with 10% heat-inactivated horse serum (Gibco, 26050), 1× MEM non-essential amino acids (Gibco, 11140), 10 mM HEPES (Gibco, 15630), 100 units/mL penicillin, and 100 units/mL streptomycin) at 37° C. and 5% CO₂ in a humidified incubator. Cultures were passaged twice weekly using 10 mL of 1× Phosphate-Buffered Saline (PBS) without Ca²⁺ and Mg²⁺ (Gibco, 20012) for washing and 3-5 mL per T-175 flask of TrypLE Express Enzyme (Gibco, 12604) for dissociation of adherent cells.

*Cryptosporidium parvum* oocysts purchased from the Sterling Laboratory, University of Arizona (Iowa isolate) were purified from infected calf feces using discontinuous sucrose and cesium chloride centrifugation gradients and stored in PBS solution containing 0.01% Tween 20, 100 units/mL penicillin and 100 units/mL gentamicin.

*Cryptosporidium hominis* oocysts were purchased from the Tufts University Cummings School of Veterinary Medicine (courtesy of Dr. Saul Tzipori). *C. hominis* oocysts were purified from infected gnotobiotic piglet feces and stored in PBS solution containing 0.01% Tween-20, 100 units/mL penicillin and 100 units/mL gentamicin. *C. parvum* and *C. hominis* oocysts less than three months old from the date of shedding were used in infection experiments.

Excystaion and infection: Excystation and infection protocols were developed following established methods with some modifications (Gut & Nelson, 1999, Upton et al., 1995, Bessoff et al., 2013). Briefly, oocysts were primed in 1 mL of 10 mM hydrochloric acid in 1× Hank's Balanced Salt Solution (HBSS) (Gibco, 14025) for 10 minutes with agitation at 1000 rpm, 37° C. on an Eppendorf thermomixer, then washed twice with 1 mL of room temperature non-acidic 1× HBSS by centrifugation at 13,000 rpm for 3 minutes at 25° C. Primed oocysts were further excysted at a concentration of $1\times10^6$ oocysts/μL in parasite infection medium consisting of a pre-warmed and pre-gassed 1:1 formulation of Leibovitz's L-15 medium (Gibco, 11415) and UltraCULTURE medium (Lonza, 12-725F) supplemented with 2 mM sodium taurocholate (Sigma, 86339-1), 10% heat-inactivated horse serum, and 200 μM L-ascorbic acid (Sigma, 95210) at 25° C. for 10 minutes. HCT-8 monolayer cells were infected with excysted cryptosporidium at a specified multiplicity of infection (MOI). All dilutions for subsequent assays were performed in parasite infection medium without sodium taurocholate. Pre-excysted oocysts were enumerated microscopically using a C-Chip disposable hemocytometer (NanoEnTek, DHC-N01).

Compound and assay plate preparation: Compound powders were dissolved in neat DMSO (Fisher, D4121) to 10 mM and stored at 4° C. prior to dilution into source plates. Dilutions were carried out using a Microlab STAR liquid handler (Hamilton) to obtain compound source plates containing the ten-point or eight-point three fold dilutions starting from 10 mM in duplicates. Source plates were stored at 4° C. prior to spotting into assay plates. Before administration, all compound source plates were equilibrated to room temperature. A specified volume of compounds from source plate were spotted to assay plate using an Echo Acoustic liquid handler (LABCYTE, 550) so that the final DMSO concentration was less than 0.5%. Each assay plate a specified number of DMSO-treated negative control wells and a well-studied potent active compound at 100 nM as positive control. As a quality control, all positive and negative-control wells were used to calculate a Z'-value and signal to noise ratio (S:N) for each plate.

$IC_{50}$ Determination by Cytopathic Effect (CPE) Based Assay:

Cryptosporidium spp are obligate-intracellular parasites that infect intestinal epithelial cells and the host cell is killed upon parasite egress. In patients, cryptosporidium infection has been shown to induce severe villous atrophy caused by the loss of villous enterocytes. The loss of epithelial cells is due to both rapid parasite invasion/multiplication/egress and also pro-inflammatory immune response (Adams et al., 1994, Griffiths et al., 1994). We have observed a consistent cytopathic effect (CPE) in HCT-8 cells with C. spp infection the loss of viability of the host cells using CellTiter-Glo reagent.

Confluent HCT-8 cells in T-175 flasks were directly infected with excysted oocysts at an MOI (host to parasite) of 1:2 for C. parvum and 1:4 for C. hominis. The number of host-cells is determined using a NucleoCounter (Chemometec, NC-100) in a control flask. Infected monolayers were incubated for 3 hours at 37° C., followed by gentle washing once with 10 mL of 1×PBS before dissociation with 3-5 mL of TrypLE. Infected cell pellet was re-suspended in 90% complete growth medium and 10% parasite infection medium without sodium taurocholate. $2.5 \times10^4$ batch-infected HCT-8 cells were seeded in each well of a 384-well plate (Greiner, 789091) in a total well volume of 30 μL using a MultiDrop liquid handler (ThermoScientific, 5840300). All plates were incubated for 24 hours at 37° C. prior to compound administration. Compounds were spotted at various concentrations at 60 nL per well from the source plates using an Echo Acoustic liquid handler (LABCYTE, 550) and treatment allowed to proceed for 48 hours. Following compound treatment, assay plates were allowed to equilibrate to room temperature for one hour in a biosafety cabinet to minimize temperature gradient effects. Cells were lysed and host cell viability measured by addition of 20 μL per well of Cell-Titer Glo 2.0 (Promega, G9243) using the Multidrop. The luminescence reading was measured at the rate of 0.1 seconds per well by a Clarity Luminometer (BioTek). Raw data files were exported and results were expressed as percent stimulation where 100% stimulation was equal to the mean of the active control wells and 0% stimulation was equal to the mean of the DMSO-treated negative control wells. Cell viability curves were analyzed using Novartis software.

The effectiveness of selected compounds to minimize the cytopathic effect of both Cryptosporidium hominis and Cryptosporidium parvum were measured. The result were reported in Table II, C. parvum in the first column [(Cp CPE $EC_{50}$ (μM)] and C. hominis in the fourth column. [(Ch CPE $EC_{50}$ (μM)]. The effectiveness ranges from no effect to nanomolar concentration.

$IC_{50}$ Determination by High Content Imaging (HCI) Assay:

Infection and compound treatment: Imaging assays were developed following established Cryptosporidium spp labeling and in vitro infection models with some modifications (Bessoff et al., 2013, Gut & Nelson, 1999). Briefly, $2\times10^4$ HCT-8 cells per well were seeded into 384-well, flat black clear-bottom OPERA assay plates (Greiner, 789071-G) at 20 μL per well in complete growth medium using a Multidrop Combi liquid handler (ThermoScientific, 5840300) and standard tube dispensing cassette (ThermoScientific, 24072670) and incubated for 24 hours at 37° C. The HCT-8 cells were infected with 10 μL per well of $1\times10^4$ excysted C. parvum oocysts (host to parasite MOI of 1:0.5) or 10 μL per well of $4\times10^4$ excysted C. hominis oocysts (MOI 1:2) in parasite infection medium using the Multidrop and incubated at 37° C. 24 hours post-infection, 60 nL of compounds were spotted in each well using an Echo Acoustic liquid handler (LABCYTE, 550) as described above and the plates were incubated for 48 hours at 37° C.

Fixation and labeling: Following compound treatment, cells were washed twice with PBS, fixed with 40 μL of 4% paraformaldehyde (Electron Microscopy Sciences, 15710) in PBS for 20 minutes at 25° C. and washed with PBS followed by PBS-FT (PBS containing 1% fetal bovine serum in PBS and 0.05% Tween-20. To ensure monolayers are uncompromised, all aspiration steps were performed allowing for a 15 μL remaining well volume. The fixed cells were permeabilized and blocked PBS-FT for 30 minutes at 25° C. For staining 4 μg/mL Streptavidin-conjugated Alexa Fluor 568 (Life Technologies, S11226) was mixed with 2 μg/mL biotinylated Vicia villosa lectin (Vector Laboratories, B-1235) in PBS-FT and incubated at 25° C. for 1 hour. The bound label was filtered through a pre-equilibrated syringe filter (Sartorius Stedim, 16534-K). To label the intracellular parasitic life stages the permeabilized cells were incubated with 20 μL Alexa568-VVL for 1 hour at 25° C. The labelled cells were washed with PBS-FT followed by a PBS wash. Finally HCT-8 host cell nuclei were counterstained with 5 μM Draq-5 (Abcam, ab108410) diluted in PBS and stored before detection.

Detection: Once labeled, the plates were imaged using an Opera QEHS (PerkinElmer™).

Imaging was performed at 10× using a Nikon UPlan Apo lens. Nine images were collected in each well covering more than 80% of the well surface. The samples were exposed to 561 nm and 635 nm laser lines to excite respectively the Alexa Fluor®598 conjugated lectins and DRAQ5™. The laser power was selected at 2250 µW, exposure time set at 800 milliseconds and focal height set at 5 µm. The fluorescence signal was then collected on cooled CCD cameras after passing the emitted light through a quad-band primary dichroic (405/488/561/635) and a detection dichroic (510) followed by emission filers 600/40 and a 690/50 to collect the light emitted respectively by the labeled parasite and nuclei.

Analysis: Images were analyzed using a custom analysis script written in Acapella® (PerkinElmer™). In brief, nuclei were detected and the mask obtained was then dilated to encompass the cell cytoplasm. These objects were thereafter referred as cell-bodies. The average signal from the images collected for the parasite channel was measured for each cell body. Cells were then classified as infected vs. not-infected by applying an intensity cut-off and for each well the number of cells and the percentage of infected cells was calculated. The cut-off used to classify the cells as infected vs. not infected was automatically optimized using the positive and negative controls, using an 'R' (Team, 2015). In brief, the cut-off was set as the intensity threshold which maximized the Z' factor (Zhang et al., 1999). Results were expressed as percent inhibition where 100% inhibition was equal to the mean of the active control wells and 0% inhibition was equal to the mean of the DMSO-treated negative control wells. The data was analyzed with the Novartis in-house software (Helios software application, Novartis Institutes for BioMedical Research, unpublished) using the methods described in the following references (Fomenko et al., 2006, Kelly & Rice, 1990, Normolle, 1993, Sebaugh, 2011) (Kahm et al., 2010). After manual curation to address any potential screening patterns or artifacts, each well data point was normalized using the control wells so that no effect was set to 0% and full inhibition was set to −100%. The data was then curve fitted in Helios software to calculate the active concentration which resulted in having only 50% of the cells infected.

The result of the assay of selected compounds on *C. parvum* were reported on the Table II, second column [Cp HCl $IC_{50}$ (µM)] Selected compounds exhibit sub-micro molar activities in preventing infection of the host cells.

Determination of Cytotoxicity

Cytotoxicity against HepG2 (ATCC #HB-8065), a human liver cancer cell line, was determined as previously described earlier (Manjunatha et al., 2015). Briefly, cells were seeded at a density of $10^5$ cells per well, incubated at 37° C. for 24 h and exposed to two-fold serially-diluted compounds for 5 days. Cell viability was monitored using the Cell Proliferation Kit II (Invitrogen).

The cytotoxicity values of selected compounds are reported in the fifth column [HepG2 $CC_{50}$ (µM)] of Table II. The results show the compounds are generally safe.

PI(4)K Enzymatic Assay

Baculovirus expression and purification of *C. parvum* phosphatidylinositol 4-kinase: The full-length coding sequence of *C. parvum* PI(4)K (cgd8_4500, 1114 amino acids) was codon-optimized for baculovirus expression, synthesized and cloned into pFastBac-HTb (Invitrogen 10584-027) in frame with the amino-terminal polyhistidine tag using the BamHI and HindIII restriction sites. Recombinant pFastBacHTb-CpPI(4)K bacmid clones were generated by site-specific transposition in *E. coli* DH10Bac (Invitrogen 10361-012). The bacmid sequence was confirmed by direct DNA sequencing to confirm a lack of mutations across the whole gene. The subsequent steps for bacmid isolation, transfection and selection of the recombinant viruses were performed according to the manufacturer's protocol (Bac-to-Bac system #10359, Invitrogen).

SF9 cells, cultured in SF-900 µl serum-free medium, were transfected with recombinant baculovirus at 1/200 (v/v) and incubated at 27° C. for 72 h. The pellets were collected after centrifugation and re-suspended in cell lysis buffer (20 mM Tris-HCl, pH 7.5, 300 mM NaCl, 1 mM DTT, 20 mM imidazole, 0.01% Triton X-100 and 1× complete protease inhibitor cocktail without EDTA (Roche Diagnostics 04693116001)). The cell suspension was lysed by sonication and the clarified supernatant was loaded onto a 1 ml HisTrap affinity column (GE Healthcare) pre-equilibrated with buffer A (20 mM Tris-HCl, pH 7.5, 300 mM NaCl, 1 mM DTT, 20 mM Imidazole, and 1× complete protease inhibitor cocktail without EDTA). The column was washed with buffer B (buffer A containing 45 mM imidazole) and the bound protein of interest was eluted with buffer C (buffer A with 90 mM imidazole). The fractions containing CpPI(4)K were pooled, concentrated using Amicon Ultra-15 and purified by a gel-filtration column (Hi-Load 26/60 Superdex 200, GE Healthcare) equilibrated with 20 mM Tris, pH 7.5, 300 mM NaCl, 1 mM DTT and 1× protease inhibitor cocktail without EDTA. The concentrations of the purified protein (Mw 132.39 kda) was determined by using the protein molar extinction coefficient ($\varepsilon_{280\ nm}$=133,810 $M^{-1}$ $cm^{-1}$). Aliquots were flash frozen in liquid nitrogen and immediately stored at −80° C.

PI(4)K enzymatic Assay The CpPI(4)K enzymatic assay was performed as described earlier with a some modifications (McNamara et al., 2013). Briefly, L-α-phosphatidylinositol (Avanti Polar Lipid 840046), dissolved in 3% n-octylglucoside (Roche Diagnostics 10634425001), was used as the lipid substrate for the PI(4)K activity assay. CpPI(4)K was assayed using Transcreener $ADP_2$ FP detection kit (BellBrook 3010) in a black, solid 384-well plate (Corning 3575). The final assay volume was 10 µl and contained 3 nM of the respective CpPI(4)K construct in 10 mM Tris, pH 7.5, 1 mM DTT, 3 µM ATP, 5 mM Mn2+, 0.05% Triton X-100 and 10 µM phosphatidylinositol/octylglucoside. The enzyme reaction was performed for 50 minutes at room temperature and was stopped by adding 10 µl of detection mix containing 1× stop buffer (50 mM HEPES, pH7.5, 400 mM NaCl, 20 mM EDTA, and 0.02% Brij-35), 2 nM AMP Alexa Fluor 633 tracer, and 20 µg $ml^{-1}$ ADP antibody. Fluorescence polarization measurements were performed on the Infinite M1000 plate reader (Tecan) with λex=635 nm and λem=680 nm (20-nm bandwidth). $IC_{50}$ values were calculated using Graphpad Prism software.

These compounds exhibit sub-micro molar inhibitory values and are hence potent inhibitors of *C. parvum* PI(4)K enzyme.

The resulted $IC_{50}$ values are summarized in Table 2 below: +≥1 µM; 1 µM>++≥0.1 µM; 0.1 µM>+++

| Ex # | Compound name | (a) C.p.* PI(4)K IC$_{50}$ (μM) | (b) C.p.* CPE EC$_{50}$ (μM) | (c) C.h.* CPE EC$_{50}$ (μM) | (d) H.s.* PI(4)K IC$_{50}$ (μM) |
|---|---|---|---|---|---|
| 1.01 | Methyl 5-((tert-butoxycarbonyl)amino)-2-chlorobenzoate | +++ | +++ | +++ | ++ |
| 1.02 | tert-Butyl 5-(3-(4-carbamoylphenyl)-N-methylpyrazolo[1,5-a]pyridine-5-carboxamido)-2-chlorobenzoate | +++ | ++ | | |
| 1.03 | 5-(3-(4-Carbamoylphenyl)-N-methylpyrazolo[1,5-a]pyridine-5-carboxamido)-2-chlorobenzoic acid | +++ | + | | ++ |
| 1.04 | 2-(Methylthio)ethyl 5-(3-(4-carbamoylphenyl)-N-methylpyrazolo[1,5-a]pyridine-5-carboxamido)-2-chlorobenzoate | +++ | + | | |
| 1.05 | Isobutyl 5-(3-(4-carbamoylphenyl)-N-methylpyrazolo[1,5-a]pyridine-5-carboxamido)-2-chlorobenzoate | +++ | ++ | | |
| 1.06 | 2-Methoxy-2-oxoethyl 5-(3-(4-carbamoylphenyl)-N-methylpyrazolo[1,5-a]pyridine-5-carboxamido)-2-chlorobenzoate | +++ | + | | |
| 1.07 | Thiazol-5-ylmethyl 5-(3-(4-carbamoylphenyl)-N-methylpyrazolo[1,5-a]pyridine-5-carboxamido)-2-chlorobenzoate | +++ | ++ | | |
| 1.08 | 2-Morpholinoethyl 5-(3-(4-carbamoylphenyl)-N-methylpyrazolo[1,5-a]pyridine-5-carboxamido)-2-chlorobenzoate | +++ | ++ | | + |
| 1.09 | Ethyl 5-(3-(4-carbamoylphenyl)-N-methylpyrazolo[1,5-a]pyridine-5-carboxamido)-2-chlorobenzoate | +++ | ++ | | |
| 1.10 | 2,2,2-Trifluoroethyl 5-(3-(4-carbamoylphenyl)-N-methylpyrazolo[1,5-a]pyridine-5-carboxamido)-2-chlorobenzoate | +++ | + | | |
| 1.11 | 2-Methoxyethyl 5-(3-(4-carbamoylphenyl)-N-methylpyrazolo[1,5-a]pyridine-5-carboxamido)-2-chlorobenzoate | +++ | ++ | | |
| 1.12 | 2-(Dimethylamino)-2-oxoethyl 5-(3-(4-carbamoylphenyl)-N-methylpyrazolo[1,5-a]pyridine-5-carboxamido)-2-chlorobenzoate | +++ | ++ | | |
| 1.13 | Isopropyl 5-(3-(4-carbamoylphenyl)-N-methylpyrazolo[1,5-a]pyridine-5-carboxamido)-2-chlorobenzoate | +++ | ++ | | |
| 1.14 | rac-1-((Ethoxycarbonyl)oxy)ethyl 5-(3-(4-carbamoylphenyl)-N-methylpyrazolo[1,5-a]pyridine-5-carboxamido)-2-chlorobenzoate | ++ | + | | + |
| 1.15 | rac-(Tetrahydrofuran-2-yl)methyl 5-(3-(4-carbamoylphenyl)-N-methylpyrazolo[1,5-a]pyridine-5-carboxamido)-2-chlorobenzoate | +++ | ++ | | |
| 1.16 | Methyl 2-chloro-5-(N-methyl-3-(4-(methylcarbamoyl)phenyl)pyrazolo[1,5-a]pyridine-5-carboxamido)benzoate | +++ | +++ | +++ | ++ |
| 1.17 | t-Butyl 2-chloro-5-(N-methyl-3-(4-(methylcarbamoyl)phenyl)pyrazolo[1,5-a]pyridine-5-carboxamido)benzoate | +++ | +++ | | |
| 1.18 | 2-Chloro-5-(N-methyl-3-(4-(methylcarbamoyl)phenyl)pyrazolo[1,5-a]pyridine-5-carboxamido)benzoic acid | +++ | + | | ++ |
| 1.19 | 2-Morpholinoethyl 2-chloro-5-(N-methyl-3-(4-(methylcarbamoyl)phenyl)pyrazolo[1,5-a]pyridine-5-carboxamido)benzoate | +++ | ++ | | ++ |
| 1.20 | (5-Methyl-2-oxo-1,3-dioxol-4-yl)methyl 2-chloro-5-(N-methyl-3-(4-(methylcarbamoyl)phenyl)pyrazolo[1,5-a]pyridine-5-carboxamido)benzoate | | | | |
| 1.21 | Methyl 2-chloro-5-(N-methyl-3-(2-methyl-4-(carbamoyl)phenyl)pyrazolo[1,5-a]pyridine-5-carboxamido)benzoate | +++ | ++ | | + |

-continued

| Ex # | Compound name | (a) C.p.* PI(4)K IC$_{50}$ (μM) | (b) C.p.* CPE EC$_{50}$ (μM) | (c) C.h.* CPE EC$_{50}$ (μM) | (d) H.s.* PI(4)K IC$_{50}$ (μM) |
|---|---|---|---|---|---|
| 1.22 | Methyl 2-chloro-5-(N-methyl-3-(3-methyl-4-(carbamoyl)phenyl)pyrazolo[1,5-a]pyridine-5-carboxamido)benzoate | ++ | + | | + |
| 1.23 | Methyl 5-(3-(4-carbamoylphenyl)pyrazolo[1,5-a]pyridine-5-carboxamido)-2-chlorobenzoate | + | + | | + |
| 1.24 | Methyl 2-chloro-5-(3-(4-(methylcarbamoyl)phenyl)pyrazolo[1,5-a]pyridine-5-carboxamido)benzoate | + | + | | + |
| 1.25 | Methyl 5-(3-(4-carbamoylphenyl)-N-methylpyrazolo[1,5-a]pyridine-5-carboxamido)-2-(trifluoromethoxy)benzoate | +++ | ++ | | + |
| 1.26 | Methyl 5-(N-methyl-3-(4-(methylcarbamoyl)phenyl)pyrazolo[1,5-a]pyridine-5-carboxamido)-2-(trifluoromethoxy)benzoate | +++ | ++ | | |
| 1.27 | Methyl 5-(3-(4-carbamoylphenyl)-N-methylpyrazolo[1,5-a]pyridine-5-carboxamido)-2-cyanobenzoate | +++ | +++ | | + |
| 2.1 | Methyl 2-chloro-5-(N-methyl-3-(4-(methylcarbamoyl)phenyl)imidazo[1,2-a]pyrazine-6-carboxamido)benzoate | +++ | ++ | | + |
| 3.1 | Methyl 2-chloro-5-(N-methyl-3-(4-(methylcarbamoyl)phenyl)pyrazolo[1,5-c]pyrimidine-5-carboxamido)benzoate | +++ | ++ | ++ | + |
| 4.1 | Methyl 2-(3-(4-carbamoylphenyl)-N-methylpyrazolo[1,5-a]pyridine-5-carboxamido)-5-chlorobenzoate | +++ | +++ | +++ | ++ |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound according to Formula Ia,

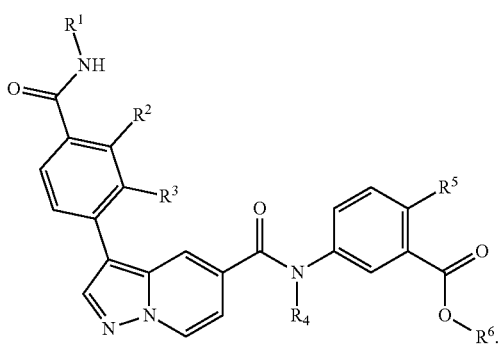

Ia or a pharmaceutically acceptable salt, tautomer or stereoisomer thereof, wherein each of $R^1$, $R^2$, $R^3$ or $R^4$ is independently hydrogen or $C_{1-6}$ alkyl;

$R^5$ is halo;

$R^6$ is selected from the group consisting of:
a) hydrogen, and
b) $C_{1-6}$ alkyl, unsubstituted or substituted by 1-3 substituents independently selected from the group consisting of
   i) $C_{1-6}$ alkoxy,
   ii) halo,
   iii) thio $C_{1-6}$ alkyl,
   iv) $C_{4-6}$ heterocycloalkyl, unsubstituted or substituted by 1-3 substituents independently selected from the group consisting of oxo and $C_{1-6}$ alkyl;
   v) $C_{5-6}$ heteroaryl, unsubstituted or substituted by 1-3 $C_{1-6}$ alkyl substituents;
   vi) —C(O)$R^7$, and
   vii) —C(O)N$R^7R^7$, wherein each $R^7$ is independently hydrogen or $C_{1-6}$ alkyl.

2. The compound according to claim 1, wherein $R^1$f, $R^2$ and $R^3$ is hydrogen and $R^4$ is $C_{1-6}$ alkyl.

3. The compound according to claim 1, wherein $R^4$ is methyl.

4. The compound according to claim 1, wherein $R^5$ is chloro.

5. The compound according to claim 1, wherein the compound is selected from the group consisting of:

Methyl 5-(3-(4-carbamoylphenyl)-N-methylpyrazolo[1,5-a]pyridine-5-carboxamido)-2-chlorobenzoate;

tert-Butyl 5-(3-(4-carbamoylphenyl)-N-methylpyrazolo[1,5-a]pyridine-5-carboxamido)-2-chlorobenzoate;

5-(3-(4-Carbamoylphenyl)-N-methylpyrazolo[1,5-a]pyridine-5-carboxamido)-2-chlorobenzoic acid;

2-(Methylthio)ethyl 5-(3-(4-carbamoylphenyl)-N-methylpyrazolo[1,5-a]pyridine-5-carboxamido)-2-chlorobenzoate;

Isobutyl 5-(3-(4-carbamoylphenyl)-N-methylpyrazolo[1,5-a]pyridine-5-carboxamido)-2-chlorobenzoate;

2-Methoxy-2-oxoethyl 5-(3-(4-carbamoylphenyl)-N-methylpyrazolo[1,5-a]pyridine-5-carboxamido)-2-chlorobenzoate;

Thiazol-5-ylmethyl 5-(3-(4-carbamoylphenyl)-N-methylpyrazolo[1,5-a]pyridine-5-carboxamido)-2-chlorobenzoate;

2-Morpholinoethyl 5-(3-(4-carbamoylphenyl)-N-methylpyrazolo[1,5-a]pyridine-5-carboxamido)-2-chlorobenzoate;

Ethyl 5-(3-(4-carbamoylphenyl)-N-methylpyrazolo[1,5-a]pyridine-5-carboxamido)-2-chlorobenzoate;

2,2,2-Trifluoroethyl 5-(3-(4-carbamoylphenyl)-N-methylpyrazolo[1,5-a]pyridine-5-carboxamido)-2-chlorobenzoate;

2-Methoxyethyl 5-(3-(4-carbamoylphenyl)-N-methylpyrazolo[1,5-a]pyridine-5-carboxamido)-2-chlorobenzoate;

2-(Dimethylamino)-2-oxoethyl 5-(3-(4-carbamoylphenyl)-N-methylpyrazolo[1,5-a]pyridine-5-carboxamido)-2-chlorobenzoatel Isopropyl 5-(3-(4-carbamoylphenyl)-N-methylpyrazolo[1,5-a]pyridine-5-carboxamido)-2-chlorobenzoate;

rac-1-((Ethoxycarbonyl)oxy)ethyl 5-(3-(4-carbamoylphenyl)-N-methylpyrazolo[1,5-a]pyridine-5-carboxamido)-2-chlorobenzoate;

rac-(Tetrahydrofuran-2-yl)methyl 5-(3-(4-carbamoylphenyl)-N-methylpyrazolo[1,5-a]pyridine-5-carboxamido)-2-chlorobenzoate;

Methyl 2-chloro-5-(N-methyl-3-(4-(methylcarbamoyl)phenyl)pyrazolo[1,5-a]pyridine-5-carboxamido)benzoate;

t-Butyl 2-chloro-5-(N-methyl-3-(4-(methylcarbamoyl)phenyl)pyrazolo[1,5-a]pyridine-5-carboxamido)benzoate;

2-Chloro-5-(N-methyl-3-(4-(methylcarbamoyl)phenyl)pyrazolo[1,5-a]pyridine-5-carboxamido)benzoic acid;

2-Morpholinoethyl 2-chloro-5-(N-methyl-3-(4-(methylcarbamoyl)phenyl)pyrazolo[1,5-a]pyridine-5-carboxamido)benzoate;

(5-Methyl-2-oxo-1,3-dioxol-4-yl)methyl 2-chloro-5-(N-methyl-3-(4-(methylcarbamoyl)phenyl)pyrazolo[1,5-a]pyridine-5-carboxamido)benzoate;

Methyl 2-chloro-5-(N-methyl-3-(2-methyl-4-(carbamoyl)phenyl)pyrazolo[1,5-a]pyridine-5-carboxamido)benzoate;

Methyl 2-chloro-5-(N-methyl-3-(3-methyl-4-(carbamoyl)phenyl)pyrazolo[1,5-a]pyridine-5-carboxamido)benzoate;

Methyl 5-(3-(4-carbamoylphenyl)pyrazolo[1,5-a]pyridine-5-carboxamido)-2-chlorobenzoate;

Methyl 2-chloro-5-(3-(4-(methylcarbamoyl)phenyl)pyrazolo[1,5-a]pyridine-5-carboxamido)benzoate;

Methyl 2-chloro-5-(N-methyl-3-(4-(methylcarbamoyl)phenyl)imidazo[1,2-a]pyrazine-6-carboxamido)benzoate; and Methyl 2-chloro-5-(N-methyl-3-(4-(methylcarbamoyl)phenyl)pyrazolo[1,5-c]pyrimidine-5-carboxamido)benzoate.

6. The compound according to claim 1, wherein the compound is capable of inhibiting or modulating the activity of a *cryptosporidium* protozoa.

7. The compound according to claim 6, wherein the *cryptosporidium* protozoa is *Cryptosporidium hominis* or *Cryptosporidium parvum*.

8. A pharmaceutical composition comprising at least one compound according to claim 1, or a pharmaceutically acceptable salt thereof, and a pharmaceutically acceptable carrier, diluent or excipient.

9. The pharmaceutical composition according to claim 8, further comprising a second therapeutic agent.

10. A method for treating, inhibiting, ameliorating, or eradicating the pathology and/or symptomology of cryptosporidiosis caused by a *cryptosporidium* protozoa, comprising administering to a subject a therapeutically effective amount of a compound according to claim 1, wherein the administering may be in combination with a second agent.

11. The method of claim 10, wherein the crypotosporidium protozoa is *Cryptosporidium hominis* or *Cryptosporidium parvum*.

12. The compound according to claim 1, wherein said compound is methyl 5-(3-(4-carbamoylphenyl)-N-methylpyrazolo[1,5-a]pyridine-5-carboxamido)-2-chlorobenzoate.

13. The compound according to claim 1, wherein said compound is methyl 2-chloro-5-(N-methyl-3-(4-(methylcarbamoyhphenyl)pyrazolo[1,5-a]pyridine-5-carboxamido)benzoate.

14. The compound according to claim 1, wherein said compound is 2-chloro-5-(N-methyl-3-(4-(methylcarbamoyhphenyl)pyrazolo[1,5-a]pyridine-5-carboxamido)benzoic acid.

15. The compound according to claim 1, wherein said compound is methyl 2-chloro-5-(3-(4-(methylcarbamoyhphenyhpyrazolo[1,5-a]pyridine-5-carboxamido)benzoate.

* * * * *